United States Patent
Yoshida et al.

(10) Patent No.: US 10,065,995 B2
(45) Date of Patent: *Sep. 4, 2018

(54) PROTEIN FOR AFFINITY-SEPARATION MATRIX

(75) Inventors: Shinichi Yoshida, Takasago (JP); Dai Murata, Takasago (JP); Shunichi Taira, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/007,225

(22) PCT Filed: Mar. 26, 2012

(86) PCT No.: PCT/JP2012/057824
§ 371 (c)(1),
(2), (4) Date: Dec. 6, 2013

(87) PCT Pub. No.: WO2012/133349
PCT Pub. Date: Oct. 4, 2012

(65) Prior Publication Data
US 2014/0107315 A1      Apr. 17, 2014

(30) Foreign Application Priority Data

Mar. 25, 2011 (JP) ................................. 2011-068498

(51) Int. Cl.
| | | |
|---|---|---|
| *C07K 14/31* | (2006.01) | |
| *C07K 1/22* | (2006.01) | |
| C07K 16/00 | (2006.01) | |
| C07K 16/12 | (2006.01) | |
| C07K 17/12 | (2006.01) | |
| B01D 15/38 | (2006.01) | |
| C07K 16/06 | (2006.01) | |
| C07K 17/00 | (2006.01) | |

(52) U.S. Cl.
CPC .............. *C07K 14/31* (2013.01); *C07K 1/22* (2013.01); *B01D 15/3809* (2013.01); *B01J 2220/4856* (2013.01); *C07K 16/00* (2013.01); *C07K 16/065* (2013.01); *C07K 16/1271* (2013.01); *C07K 17/00* (2013.01); *C07K 17/12* (2013.01); *C07K 2317/21* (2013.01); *C07K 2317/52* (2013.01); *C07K 2317/92* (2013.01)

(58) Field of Classification Search
CPC .. A61K 2300/00; A61K 38/164; C07K 14/31; C07K 1/22; C07K 1/20; C07K 16/00; C07K 16/065; C07K 16/1271; C07K 17/00; C07K 17/12; C07K 2317/21; C07K 2317/52; C07K 2317/92
See application file for complete search history.

(56) References Cited

U.S. PATENT DOCUMENTS

| | | | |
|---|---|---|---|
| 6,013,763 A | 1/2000 | Braisted et al. | |
| 6,103,763 A | 8/2000 | Horst | |
| 9,284,354 B2 | 3/2016 | Yoshida et al. | |
| 2008/0108564 A1 | 5/2008 | Holmes et al. | |
| 2009/0299035 A1 | 12/2009 | Iwakura et al. | |
| 2010/0158847 A1 | 6/2010 | Fahnestock et al. | |
| 2010/0286373 A1* | 11/2010 | Majima et al. | ............ 530/387.2 |
| 2012/0208234 A1 | 8/2012 | Yoshida et al. | |
| 2013/0096276 A1 | 4/2013 | Yoshida et al. | |
| 2014/0107315 A1 | 4/2014 | Yoshida et al. | |

FOREIGN PATENT DOCUMENTS

| | | |
|---|---|---|
| EP | 1992692 A1 | 11/2008 |
| EP | 2690173 A1 | 1/2014 |
| JP | 2007-252368 A | 10/2007 |
| JP | 2008-115151 A | 5/2008 |
| JP | 2008-266219 A | 11/2008 |
| WO | WO-1997/017361 A1 | 5/1997 |
| WO | WO-2008/044692 A1 | 4/2008 |
| WO | WO-2010/110288 A1 | 9/2010 |
| WO | WO-2011/118699 A1 | 9/2011 |
| WO | WO-2012/133349 A1 | 10/2012 |

OTHER PUBLICATIONS www.russelllab.org/aas/lys.html, Lysine, pp. 1-2, published online Oct. 1, 2002.*
The On-line Medical Dictionary, Definition of Derivative, p. 3, published online Nov. 18, 1997.*
Sriram Sokalingam, A Study on the Effect of Surface Lysine to Arginine Mutagenesis on Protein Stability and Structure Using Green Fluorescent Protein, PLoS ONE 7(7): e40410. doi:10.1371/journal.pone.0040410, 2012.*
Francesca Scaramozzini et al., Improvement of Catalytic Properties of *Escherichia coli* Penicillin G Acylase Immobilized on Glyoxyl Agarose by Addition of a Six-Amino-Acid Tag, Applied and Environmental Microbiology, Dec. 2005, vol. 71, No. 12, pp. 8937-8940.
International Preliminary Report on Patentability (Chapter 1) issued in PCT/JP2012/057824, dated Oct. 2, 2013, English translation.

(Continued)

*Primary Examiner* — Rachael E Bredefeld
*Assistant Examiner* — Erinne R Dabkowski
(74) *Attorney, Agent, or Firm* — Polsinelli PC

(57) ABSTRACT

An object of the present invention is to provide a technique to create novel engineered protein ligands that, when immobilized through a lysine residue (its side chain ε-amino group) which allows for efficient immobilization to a carrier, show the optimum binding capacity and binding efficiency to a target molecule. The present invention provides an engineered protein having a sequence obtained by replacing all the lysine residues in Protein A, which is the most typical protein ligand, with other amino acids, and adding lysine at a terminal; and an affinity separation matrix in which such an engineered protein is immobilized on a water-insoluble carrier by reductive amination or the like. This affinity separation matrix is characterized by its high binding capacity to a target molecule even when the immobilized amount of the ligand is small.

13 Claims, 2 Drawing Sheets

Specification includes a Sequence Listing.

(56) References Cited

OTHER PUBLICATIONS

Yoshida et al., "Rational design and engineering of protein A to obtain the controlled elution profile in monoclonal antibody purification", Chem-Bio Informatics Journal, 2012, vol. 2, p. 1-13.
Hober et al., "Protein A chromatography for antibody purification", Journal of Chromatography B, 848 (2007) 40-47.
Low et al., "Future of antibody purification", Journal of Chromatography B, 848 (2007) 48-63.
Roque et al., "Affinity-based methodologies and ligands for antibody purification: Advances and perspectives", Journal of Chromatography A, 1160 (2007) 44-55.
Wong et al., "Selective Covalent Protein Immobilization: Strategies and Applications", Chem. Rev. 2009, 109, 4025-4053.
Ljungquist et al., "Thiol-directed immobilization of recombinant IgG-binding receptors", Eur. J. Biochem. 186, 557-561 (1989).
English translation of International Preliminary Report on Patentability dated Mar. 24, 2015 in PCT/JP2013/075656.

* cited by examiner

```
          1         10        20        30        40        50
E      AQHDEA------QV-N-----NAD----------Q-ANV-G--Q----S-----
D      ADAQQ------D--S-----NM---N-------Q-TNV-G------ES------
A      ----N--------------NM---N--------Q-ANL--------ES------
B      ------------------N-------------Q-ANL-----------------
C      ADNKFNKEQQNAFYEILHLPNLTEEQRNGFIQSLKDDPSVSKEILAEAKKLNDAQAPK
```

SEQ ID Nos: 1-5 correspond to the sequences in Fig 1. Domain E–SEQ ID NO. 1; Domain D–SEQ ID NO. 2; Domain A–SEQ ID NO. 3; Domain B–SEQ ID NO.4; Domain C–SEQ ID NO. 5.

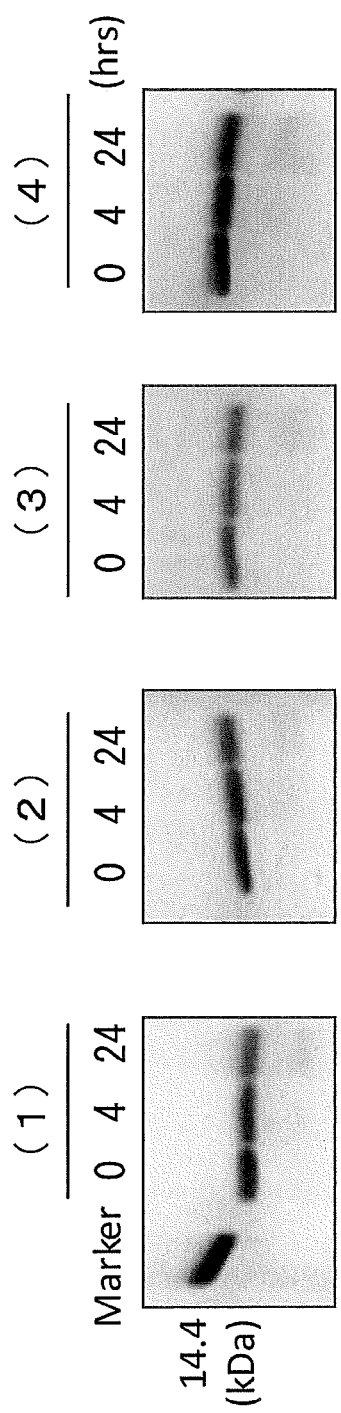

SEQUENCE LISTING

<160> NUMBER OF SEQ ID NOS: 97

<210> SEQ ID NO 1
<211> LENGTH: 56
<212> TYPE: PRT
<213> ORGANISM: Staphylococcus aureus

<400> SEQUENCE: 1

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 2
<211> LENGTH: 61
<212> TYPE: PRT
<213> ORGANISM: Staphylococcus aureus

<400> SEQUENCE: 2

Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 6
<211> LENGTH: 72
<212> TYPE: DNA
<213> ORGANISM: Artificial Sequence
<220> FEATURE:
<223> OTHER INFORMATION: synthetic oligonucleotide

<400> SEQUENCE: 6
cgtggatccg ctgacaaccg tttcaacgag gaacaacaaa atgctttcta tgaaattta     60 catttaccta ac                                                       72

<210> SEQ ID NO 7
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 7
gtgcaagctt tggatgaagg cgttacgttg ttcttcagtt aagttaggta atgtaaaat     60 ttcatagaaa gc                                                       72

<210> SEQ ID NO 8
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 8
caaagcttgc acgacgatcc ttcagtgagc cgcgaaattt agcagaagc tcagcgccta     60

<210> SEQ ID NO 9
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 9
cgatgaattc taggatcctg gtgcttgagc atcgtttagg cgctgagctt ctgctaaaat    60

<210> SEQ ID NO 10
<211> LENGTH: 58
<212> TYPE: PRT

```
<213> ORGANISM: Artificial Sequence
<220> FEATURE:
<223> OTHER INFORMATION: SpA C domain mutant

<400> SEQUENCE: 10

Ala Asp Asn Arg Phe Asn Glu Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu His Asp Asp Pro Ser Val Ser Arg Glu Ile Leu Ala Glu Ala
        35                  40                  45

Gln Arg Leu Asn Asp Ala Gln Ala Pro Gly
    50                  55

<210> SEQ ID NO 11
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 11
caaccgtttc aacgacgaac aacaaaatg                                  29

<210> SEQ ID NO 12
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 12
cattttgttg ttcgtcgttg aaacggttg                                  29

<210> SEQ ID NO 13
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 13
caaccgtttc aaccgggaac aacaaaatg                                  29

<210> SEQ ID NO 14
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 14
cattttgttg ttcccggttg aaacggttg                                  29

<210> SEQ ID NO 15
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 15
catccaaagc ttgcgcgacg atccttcag                                  29
```

```
<210> SEQ ID NO 16
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 16
ctgaaggatc gtcgcgcaag ctttggatg                              29

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 17
gcagaagctc ggcgcctaaa c                                      21

<210> SEQ ID NO 18
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 18
gtttaggcgc cgagcttctg c                                      21

<210> SEQ ID NO 19
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 19
gcagaagctc ggcacctaaa cgatg                                  25

<210> SEQ ID NO 20
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 20
catcgtttag gtgccgagct tctgc                                  25

<210> SEQ ID NO 21
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 21

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg Arg Leu Asn Asp Ala Gln Ala Pro Gly
```

<210> SEQ ID NO 22
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 22

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Gln Arg Leu Asn Asp Ala Gln Ala Pro Gly
    50                  55

<210> SEQ ID NO 23
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 23

Ala Asp Asn Arg Phe Asn Glu Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg His Leu Asn Asp Ala Gln Ala Pro Gly
    50                  55

<210> SEQ ID NO 24
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 24

Ala Asp Asn Arg Phe Asn Asp Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg His Leu Asn Asp Ala Gln Ala Pro Gly
    50                  55

<210> SEQ ID NO 25
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 25

Ala Asp Asn Arg Phe Asn Glu Glu Gln Gln Asn Ala Phe Tyr Glu Ile

```
  1               5                  10                  15
Leu His Leu Pro Asn Leu Thr Glu Glu Gln Arg Asn Ala Phe Ile Gln
                20                  25                  30

Ser Leu Arg Asp Asp Pro Ser Val Ser Arg Glu Ile Leu Ala Glu Ala
            35                  40                  45

Arg Arg Leu Asn Asp Ala Gln Ala Pro Gly
        50                  55
```

<210> SEQ ID NO 26
<211> LENGTH: 174
<212> TYPE: DNA
<213> ORGANISM: Artificial Sequence
<220> FEATURE:
<223> OTHER INFORMATION: Code DNA

<400> SEQUENCE: 26

```
gcagacaacc gtttcaaccg ggaacaacaa aatgctttct atgaaatttt acatttacct    60
aacttaactg aagaacaacg taacgccttc atccaaagct tgcgcgacga tccttcagtg   120
agccgcgaaa ttttagcaga agctcggcgc ctaaacgatg ctcaagcacc agga         174
```

<210> SEQ ID NO 27
<211> LENGTH: 174
<212> TYPE: DNA
<213> ORGANISM: Artificial Sequence
<220> FEATURE:
<223> OTHER INFORMATION: Code DNA

<400> SEQUENCE: 27

```
gcagacaacc gtttcaaccg ggaacaacaa aatgctttct atgaaatttt acatttacct    60
aacttaactg aagaacaacg taacgccttc atccaaagct tgcgcgacga tccttcagtg   120
agccgcgaaa ttttagcaga agctcagcgc ctaaacgatg ctcaagcacc agga         174
```

<210> SEQ ID NO 28
<211> LENGTH: 174
<212> TYPE: DNA
<213> ORGANISM: Artificial Sequence
<220> FEATURE:
<223> OTHER INFORMATION: Code DNA

<400> SEQUENCE: 28

```
gcagacaacc gtttcaacga ggaacaacaa aatgctttct atgaaatttt acatttacct    60
aacttaactg aagaacaacg taacgccttc atccaaagct tgcgcgacga tccttcagtg   120
agccgcgaaa ttttagcaga agctcggcac ctaaacgatg ctcaagcacc agga         174
```

<210> SEQ ID NO 29
<211> LENGTH: 174
<212> TYPE: DNA
<213> ORGANISM: Artificial Sequence
<220> FEATURE:
<223> OTHER INFORMATION: Code DNA

<400> SEQUENCE: 29

```
gcagacaacc gtttcaacga cgaacaacaa aatgctttct atgaaatttt acatttacct    60
aacttaactg aagaacaacg taacgccttc atccaaagct tgcgcgacga tccttcagtg   120
agccgcgaaa ttttagcaga agctcggcac ctaaacgatg ctcaagcacc agga         174
```

<210> SEQ ID NO 30
<211> LENGTH: 174
<212> TYPE: DNA

-continued

<213> ORGANISM: Artificial Sequence
<220> FEATURE:
<223> OTHER INFORMATION: Code DNA

<400> SEQUENCE: 30
gcagacaacc gtttcaacga ggaacaacaa aatgctttct atgaaatttt acatttacct      60
aacttaactg aagaacaacg taacgccttc atccaaagct tgcgcgacga tccttcagtg     120
agccgcgaaa ttttagcaga agctcggcgc ctaaacgatg ctcaagcacc agga           174

<210> SEQ ID NO 31
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 31
cgtggatctg cagacaac                                                    18

<210> SEQ ID NO 32
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 32
cacgatgaat tctatttgga tcctggtgct tgag                                  34

<210> SEQ ID NO 33
<211> LENGTH: 237
<212> TYPE: PRT
<213> ORGANISM: Artificial Sequence
<220> FEATURE:
<223> OTHER INFORMATION: SpA C domain mutant

<400> SEQUENCE: 33

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg Arg Leu Asn Asp Ala Gln Ala Pro Gly Ser Ala Asp Asn Arg Phe
    50                  55                  60

Asn Arg Glu Gln Gln Asn Ala Phe Tyr Glu Ile Leu His Leu Pro Asn
65                  70                  75                  80

Leu Thr Glu Glu Gln Arg Asn Ala Phe Ile Gln Ser Leu Arg Asp Asp
                85                  90                  95

Pro Ser Val Ser Arg Glu Ile Leu Ala Glu Ala Arg Arg Leu Asn Asp
            100                 105                 110

Ala Gln Ala Pro Gly Ser Ala Asp Asn Arg Phe Asn Arg Glu Gln Gln
        115                 120                 125

Asn Ala Phe Tyr Glu Ile Leu His Leu Pro Asn Leu Thr Glu Glu Gln
    130                 135                 140

Arg Asn Ala Phe Ile Gln Ser Leu Arg Asp Asp Pro Ser Val Ser Arg
145                 150                 155                 160

Glu Ile Leu Ala Glu Ala Arg Arg Leu Asn Asp Ala Gln Ala Pro Gly
                165                 170                 175

```
Ser Ala Asp Asn Arg Phe Asn Arg Glu Gln Gln Asn Ala Phe Tyr Glu
            180                 185                 190

Ile Leu His Leu Pro Asn Leu Thr Glu Glu Gln Arg Asn Ala Phe Ile
        195                 200                 205

Gln Ser Leu Arg Asp Asp Pro Ser Val Ser Arg Glu Ile Leu Ala Glu
    210                 215                 220

Ala Arg Arg Leu Asn Asp Ala Gln Ala Pro Gly Ser Lys
225                 230                 235
```

<210> SEQ ID NO 34
<211> LENGTH: 714
<212> TYPE: DNA
<213> ORGANISM: Artificial Sequence
<220> FEATURE:
<223> OTHER INFORMATION: Code DNA

<400> SEQUENCE: 34

```
gcagacaacc gtttcaaccg ggaacaacaa aatgctttct atgaaatttt acatttacct     60
aacttaactg aagaacaacg taacgccttc atccaaagct tgcgcgacga tccttcagtg    120
agccgcgaaa ttttagcaga agctcggcgc ctaaacgatg ctcaagcacc aggatctgct    180
gacaaccgtt tcaaccggga caacaaaat gctttctatg aaattttaca tttacctaac    240
ttaactgaag aacaacgtaa cgccttcatc caaagcttgc gcgacgatcc ttcagtgagc    300
cgcgaaattt tagcagaagc tcggcgccta aacgatgctc aagcaccagg atctgctgac    360
aaccgtttca accgggaaca acaaaatgct ttctatgaaa ttttacattt acctaactta    420
actgaagaac aacgtaacgc cttcatccaa agcttgcgcg acgatccttc agtgagccgc    480
gaaattttag cagaagctcg gcgcctaaac gatgctcaag caccaggatc tgctgacaac    540
cgtttcaacc gggaacaaca aaatgctttc tatgaaattt tacatttacc taacttaact    600
gaagaacaac gtaacgcctt catccaaagc ttgcgcgacg atccttcagt gagccgcgaa    660
attttagcag aagctcggcg cctaaacgat gctcaagcac caggatccaa atag         714
```

<210> SEQ ID NO 35
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 35

```
cgcgcgaggc agatc                                                      15
```

<210> SEQ ID NO 36
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 36

```
ccgcgtagat ctgctgacaa c                                               21
```

<210> SEQ ID NO 37
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 37

```
cccatggcta gatctgctga caac                                          24
```

<210> SEQ ID NO 38
<211> LENGTH: 232
<212> TYPE: PRT
<213> ORGANISM: Artificial Sequence
<220> FEATURE:
<223> OTHER INFORMATION: SpA C domain mutant

<400> SEQUENCE: 38

```
Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg Arg Leu Asn Asp Ala Gln Ala Pro Gly Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Gly Ala Asp Asn Arg Phe Asn Arg Glu Gln Gln Asn Ala
        115                 120                 125

Phe Tyr Glu Ile Leu His Leu Pro Asn Leu Thr Glu Glu Gln Arg Asn
    130                 135                 140

Ala Phe Ile Gln Ser Leu Arg Asp Asp Pro Ser Val Ser Arg Glu Ile
145                 150                 155                 160

Leu Ala Glu Ala Arg Arg Leu Asn Asp Ala Gln Ala Pro Gly Ala Asp
                165                 170                 175

Asn Arg Phe Asn Arg Glu Gln Gln Asn Ala Phe Tyr Glu Ile Leu His
            180                 185                 190

Leu Pro Asn Leu Thr Glu Glu Gln Arg Asn Ala Phe Ile Gln Ser Leu
        195                 200                 205

Arg Asp Asp Pro Ser Val Ser Arg Glu Ile Leu Ala Glu Ala Arg Arg
    210                 215                 220

Leu Asn Asp Ala Gln Ala Pro Lys
225                 230
```

<210> SEQ ID NO 39
<211> LENGTH: 699
<212> TYPE: DNA
<213> ORGANISM: Artificial Sequence
<220> FEATURE:
<223> OTHER INFORMATION: Code DNA

<400> SEQUENCE: 39

```
gcagacaacc gtttcaaccg ggaacaacaa atgctttct atgaaatttt acatttacct    60
aacttaactg aagaacaacg taacgccttc atccaaagct tgcgcgacga tccttcagtg   120
agccgcgaaa ttttagcaga agctcggcgc ctaaacgatg ctcaagcacc aggagctgac   180
aaccgtttca accgggaaca acaaaatgct ttctatgaaa ttttacattt acctaactta   240
actgaagaac aacgtaacgc cttcatccaa agcttgcgcg acgatccttc agtgagccgc   300
gaaattttag cagaagctcg gcgcctaaac gatgctcaag caccaggggc cgacaaccgt   360
```

```
ttcaaccggg aacaacaaaa tgctttctat gaaattttac atttacctaa cttaactgaa      420
gaacaacgta acgccttcat ccaaagcttg cgcgacgatc cttcagtgag ccgcgaaatt      480
ttagcagaag ctcggcgcct aaacgatgct caagcaccag agctgacaa ccgtttcaac       540 cgggaacaac aaaatgcttt ctatgaaatt ttacatttac taacttaac tgaagaacaa       600 cgtaacgcct tcatccaaag cttgcgcgac gatccttcag tgagccgcga aattttagca      660
gaagctcggc gcctaaacga tgctcaagca ccaaaatag                             699
```

<210> SEQ ID NO 40
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 40

```
gaattctatt tggcccctgg tgc                                              23
```

<210> SEQ ID NO 41
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 41

```
gctttcgggg ccgacaaccg                                                  20
```

<210> SEQ ID NO 42
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 42

```
ccgaatgcga attctatttt ggtgcttgag catc                                  34
```

<210> SEQ ID NO 43
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 43

```
gcaccaggag ctgacaac                                                    18
```

<210> SEQ ID NO 44
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 44

```
gttgtcagct cctggtgc                                                    18
```

<210> SEQ ID NO 45
<211> LENGTH: 18
<212> TYPE: DNA
<213> ORGANISM: Artificial Sequence
<220> FEATURE:

-continued

<223> OTHER INFORMATION: synthetic oligonucleotide

<400> SEQUENCE: 45
ctgctagcta gtgcactc                                                      18

<210> SEQ ID NO 46
<211> LENGTH: 232
<212> TYPE: PRT
<213> ORGANISM: Artificial Sequence
<220> FEATURE:
<223> OTHER INFORMATION: SpA C domain mutant

<400> SEQUENCE: 46

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Arg Ala Asp Asn Arg Phe Asn Arg Glu Gln Gln Asn Ala
        115                 120                 125

Phe Tyr Glu Ile Leu His Leu Pro Asn Leu Thr Glu Glu Gln Arg Asn
    130                 135                 140

Ala Phe Ile Gln Ser Leu Arg Asp Asp Pro Ser Val Ser Arg Glu Ile
145                 150                 155                 160

Leu Ala Glu Ala Arg Arg Leu Asn Asp Ala Gln Ala Pro Arg Ala Asp
                165                 170                 175

Asn Arg Phe Asn Arg Glu Gln Gln Asn Ala Phe Tyr Glu Ile Leu His
            180                 185                 190

Leu Pro Asn Leu Thr Glu Glu Gln Arg Asn Ala Phe Ile Gln Ser Leu
        195                 200                 205

Arg Asp Asp Pro Ser Val Ser Arg Glu Ile Leu Ala Glu Ala Arg Arg
    210                 215                 220

Leu Asn Asp Ala Gln Ala Pro Lys
225                 230

<210> SEQ ID NO 47
<211> LENGTH: 699
<212> TYPE: DNA
<213> ORGANISM: Artificial Sequence
<220> FEATURE:
<223> OTHER INFORMATION: Code DNA

<400> SEQUENCE: 47
gcagacaacc gtttcaaccg ggaacaacaa atgctttct atgaaattt acatttacct        60 aacttaactg aagaacaacg taacgccttc atccaaagct gcgcgacga tccttcagtg      120 agccgcgaaa ttttagcaga agctcggcgc ctaaacgatg ctcaagcacc acgcgctgac      180
aaccgtttca accgggaaca acaaaatgct ttctatgaaa ttttacattt acctaactta      240

```
actgaagaac aacgtaacgc cttcatccaa agcttgcgcg acgatccttc agtgagccgc    300
gaaattttag cagaagctcg gcgcctaaac gatgctcaag cacctcgagc agacaaccgt    360
ttcaaccggg aacaacaaaa tgctttctat gaaattttac atttacctaa cttaactgaa    420
gaacaacgta acgccttcat ccaaagcttg cgcgacgatc cttcagtgag ccgcgaaatt    480
ttagcagaag ctcggcgcct aaacgatgct caagcaccac gcgctgacaa ccgtttcaac    540
cgggaacaac aaaatgcttt ctatgaaatt ttacatttac taacttaac tgaagaacaa     600 cgtaacgcct tcatccaaag cttgcgcgac gatccttcag tgagccgcga aattttagca    660
gaagctcggc gcctaaacga tgctcaagca ccaaaatag                          699
```

<210> SEQ ID NO 48
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 48

```
gaattctatt tgctcgagg tgcttg                                          26
```

<210> SEQ ID NO 49
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 49

```
atggcttctc gagcagacaa ccg                                            23
```

<210> SEQ ID NO 50
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 50

```
caagcaccac gcgctgacaa ccg                                            23
```

<210> SEQ ID NO 51
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 51

```
cggttgtcag cgcgtggtgc ttg                                            23
```

<210> SEQ ID NO 52
<211> LENGTH: 232
<212> TYPE: PRT
<213> ORGANISM: Artificial Sequence
<220> FEATURE:
<223> OTHER INFORMATION: SpA C domain mutant

<400> SEQUENCE: 52

```
Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30
```

Glu Leu Arg Asp Asp Pro Ser Val Ser Arg Glu Ile Leu Ala Glu Ala
                35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Glu Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Arg Ala Asp Asn Arg Phe Asn Arg Glu Gln Gln Asn Ala
            115                 120                 125

Phe Tyr Glu Ile Leu His Leu Pro Asn Leu Thr Glu Glu Gln Arg Asn
        130                 135                 140

Ala Phe Ile Gln Glu Leu Arg Asp Asp Pro Ser Val Ser Arg Glu Ile
145                 150                 155                 160

Leu Ala Glu Ala Arg Arg Leu Asn Asp Ala Gln Ala Pro Arg Ala Asp
                165                 170                 175

Asn Arg Phe Asn Arg Glu Gln Gln Asn Ala Phe Tyr Glu Ile Leu His
            180                 185                 190

Leu Pro Asn Leu Thr Glu Glu Gln Arg Asn Ala Phe Ile Gln Glu Leu
            195                 200                 205

Arg Asp Asp Pro Ser Val Ser Arg Glu Ile Leu Ala Glu Ala Arg Arg
        210                 215                 220

Leu Asn Asp Ala Gln Ala Pro Lys
225                 230

<210> SEQ ID NO 53
<211> LENGTH: 699
<212> TYPE: DNA
<213> ORGANISM: Artificial Sequence
<220> FEATURE:
<223> OTHER INFORMATION: Code DNA

<400> SEQUENCE: 53
gcagacaacc gtttcaaccg ggaacaacaa atgctttct atgaaatttt acatttacct      60
aacttaactg aagaacaacg taacgccttc atccaagagt tgcgcgacga tccttcagtg    120
agccgcgaaa ttttagcaga agctcggcgc ctaaacgatg ctcaagcacc acgcgctgac    180
aaccgtttca ccgggaaca acaaaatgct ttctatgaaa ttttacattt acctaactta    240
actgaagaac aacgtaacgc cttcatccaa gagttgcgcg acgatccttc agtgagccgc    300
gaaattttag cagaagctcg gcgcctaaac gatgctcaag cacctcgagc agacaaccgt    360
ttcaaccggg aacaacaaaa tgctttctat gaaattttac atttacctaa cttaactgaa    420
gaacaacgta acgccttcat ccaagagttg cgcgacgatc cttcagtgag ccgcgaaatt    480
ttagcagaag ctcggcgcct aaacgatgct caagcaccac gcgctgacaa ccgtttcaac    540
cgggaacaac aaaatgcttt ctatgaaatt ttacatttac ctaacttaac tgaagaacaa    600
cgtaacgcct tcatccaaga gttgcgcgac gatccttcag tgagccgcga aattttagca    660
gaagctcggc gcctaaacga tgctcaagca ccaaaatag                            699

<210> SEQ ID NO 54
<211> LENGTH: 22
<212> TYPE: DNA
<213> ORGANISM: Artificial Sequence -continued

```
<220> FEATURE:
<223> OTHER INFORMATION: synthetic oligonucleotide

<400> SEQUENCE: 54
cttcatccaa gagttgcgcg ac                                              22

<210> SEQ ID NO 55
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 55
gtcgcgcaac tcttggatga ag                                              22

<210> SEQ ID NO 56
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 56
ccttcatcca aatcttgcgc gacg                                            24

<210> SEQ ID NO 57
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 57
cgtcgcgcaa gatttggatg aagg                                            24

<210> SEQ ID NO 58
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 58

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Ile Asp Asp Pro Ser Val Ser Arg Glu Ile Leu Ala Glu Ala
        35                  40                  45

Gln Arg Leu Asn Asp Ala Gln Ala Pro Gly
    50                  55

<210> SEQ ID NO 59
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 59

Ala Asp Asn Arg Phe Asn Asp Glu Gln Gln Asn Ala Phe Tyr Glu Ile
1               5                   10                  15

Leu His Leu Pro Asn Leu Thr Glu Glu Gln Arg Asn Ala Phe Ile Gln
```

```
                    20                  25                  30

Ser Leu Arg Asp Asp Pro Ser Val Ser Arg Glu Ile Leu Ala Glu Ala
        35                  40                  45

Gln Arg Leu Asn Asp Ala Gln Ala Pro Gly
    50                  55

<210> SEQ ID NO 60
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 60

Ala Asp Asn Arg Phe Asn Arg Glu Gln Gln Asn Ala Phe Tyr Glu Ile
1               5                  10                  15

Leu His Leu Pro Asn Leu Thr Glu Glu Gln Arg Asn Ala Phe Ile Gln
            20                  25                  30

Ser Leu Ile Asp Asp Pro Ser Val Ser Arg Glu Ile Leu Ala Glu Ala
        35                  40                  45

Arg Arg Leu Asn Asp Ala Gln Ala Pro Gly
    50                  55

<210> SEQ ID NO 61
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 61

Ala Asp Asn Arg Phe Asn Arg Glu Gln Gln Asn Ala Phe Tyr Glu Ile
1               5                  10                  15

Leu His Leu Pro Asn Leu Thr Glu Glu Gln Arg Asn Ala Phe Ile Gln
            20                  25                  30

Ser Leu His Asp Asp Pro Ser Val Ser Arg Glu Ile Leu Ala Glu Ala
        35                  40                  45

Gln Arg Leu Asn Asp Ala Gln Ala Pro Gly
    50                  55

<210> SEQ ID NO 62
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 62

Ala Asp Asn Arg Phe Asn Glu Glu Gln Gln Asn Ala Phe Tyr Glu Ile
1               5                  10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Gln Arg Leu Asn Asp Ala Gln Ala Pro Gly
    50                  55

<210> SEQ ID NO 63
<211> LENGTH: 58
<212> TYPE: PRT
<213> ORGANISM: Artificial Sequence
```

-continued

```
<220> FEATURE:
<223> OTHER INFORMATION: SpA C domain mutant

<400> SEQUENCE: 63

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu His Asp Asp Pro Ser Val Ser Arg Glu Ile Leu Ala Glu Ala
        35                  40                  45

Arg Arg Leu Asn Asp Ala Gln Ala Pro Gly
    50                  55

<210> SEQ ID NO 64
<211> LENGTH: 58
<212> TYPE: PRT
<213> ORGANISM: Artificial Sequence
<220> FEATURE:
<223> OTHER INFORMATION: SpA C domain mutant

<400> SEQUENCE: 64

Ala Asp Asn Arg Phe Asn Asp Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg Arg Leu Asn Asp Ala Gln Ala Pro Gly
    50                  55

<210> SEQ ID NO 65
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 65

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Lys
        115

<210> SEQ ID NO 66
<211> LENGTH: 116
<212> TYPE: PRT
<213> ORGANISM: Artificial Sequence
<220> FEATURE:
```

-continued

<223> OTHER INFORMATION: SpA C domain mutant

<400> SEQUENCE: 66

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Gln Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Arg Glu Ile Leu Ala Glu Ala Gln Arg Leu Asn Asp Ala
            100                 105                 110

Gln Ala Pro Lys
        115

<210> SEQ ID NO 67
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 67

Ala Asp Asn Arg Phe Asn Asp Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg His Leu Asn Asp Ala Gln Ala Pro Arg Ala Asp Asn Arg Phe Asn
    50                  55                  60

Asp Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Arg Glu Ile Leu Ala Glu Ala Arg His Leu Asn Asp Ala
            100                 105                 110

Gln Ala Pro Lys
        115

<210> SEQ ID NO 68
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 68

Ala Asp Asn Arg Phe Asn Glu Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala

```
            35                  40                  45
Arg Arg Leu Asn Asp Ala Gln Ala Pro Arg Ala Asp Asn Arg Phe Asn
     50                  55                  60
Glu Glu Gln Gln Asn Ala Phe Tyr Glu Ile Leu His Leu Pro Asn Leu
 65                  70                  75                  80
Thr Glu Glu Gln Arg Asn Ala Phe Ile Gln Ser Leu Arg Asp Asp Pro
                 85                  90                  95
Ser Val Ser Arg Glu Ile Leu Ala Glu Ala Arg Arg Leu Asn Asp Ala
                100                 105                 110
Gln Ala Pro Lys
        115
```

<210> SEQ ID NO 69
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 69

```
Ala Asp Asn Arg Phe Asn Arg Glu Gln Gln Asn Ala Phe Tyr Glu Ile
 1               5                  10                  15
Leu His Leu Pro Asn Leu Thr Glu Glu Gln Arg Asn Ala Phe Ile Gln
                 20                  25                  30
Ser Leu Ile Asp Asp Pro Ser Val Ser Arg Glu Ile Leu Ala Glu Ala
         35                  40                  45
Gln Arg Leu Asn Asp Ala Gln Ala Pro Arg Ala Asp Asn Arg Phe Asn
     50                  55                  60
Arg Glu Gln Gln Asn Ala Phe Tyr Glu Ile Leu His Leu Pro Asn Leu
 65                  70                  75                  80
Thr Glu Glu Gln Arg Asn Ala Phe Ile Gln Ser Leu Ile Asp Asp Pro
                 85                  90                  95
Ser Val Ser Arg Glu Ile Leu Ala Glu Ala Gln Arg Leu Asn Asp Ala
                100                 105                 110
Gln Ala Pro Lys
        115
```

<210> SEQ ID NO 70
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 70

```
Ala Asp Asn Arg Phe Asn Asp Glu Gln Gln Asn Ala Phe Tyr Glu Ile
 1               5                  10                  15
Leu His Leu Pro Asn Leu Thr Glu Glu Gln Arg Asn Ala Phe Ile Gln
                 20                  25                  30
Ser Leu Arg Asp Asp Pro Ser Val Ser Arg Glu Ile Leu Ala Glu Ala
         35                  40                  45
Gln Arg Leu Asn Asp Ala Gln Ala Pro Arg Ala Asp Asn Arg Phe Asn
     50                  55                  60
Asp Glu Gln Gln Asn Ala Phe Tyr Glu Ile Leu His Leu Pro Asn Leu
 65                  70                  75                  80
Thr Glu Glu Gln Arg Asn Ala Phe Ile Gln Ser Leu Arg Asp Asp Pro
                 85                  90                  95
```

Ser Val Ser Arg Glu Ile Leu Ala Glu Ala Gln Arg Leu Asn Asp Ala
            100                 105                 110

Gln Ala Pro Lys
        115

<210> SEQ ID NO 71
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 71

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Ile Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Ile Asp Asp Pro
                85                  90                  95

Ser Val Ser Arg Glu Ile Leu Ala Glu Ala Arg Arg Leu Asn Asp Ala
            100                 105                 110

Gln Ala Pro Lys
        115

<210> SEQ ID NO 72
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 72

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu His Asp Asp Pro Ser Val Ser Arg Glu Ile Leu Ala Glu Ala
        35                  40                  45

Gln Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu His Asp Asp Pro
                85                  90                  95

Ser Val Ser Arg Glu Ile Leu Ala Glu Ala Gln Arg Leu Asn Asp Ala
            100                 105                 110

Gln Ala Pro Lys
        115

<210> SEQ ID NO 73
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 73

Ala Asp Asn Arg Phe Asn Glu Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Gln Arg Leu Asn Asp Ala Gln Ala Pro Arg Ala Asp Asn Arg Phe Asn
    50                  55                  60

Glu Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Arg Glu Ile Leu Ala Glu Ala Gln Arg Leu Asn Asp Ala
            100                 105                 110

Gln Ala Pro Lys
        115

<210> SEQ ID NO 74
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 74

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu His Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu His Asp Asp Pro
                85                  90                  95

Ser Val Ser Arg Glu Ile Leu Ala Glu Ala Arg Arg Leu Asn Asp Ala
            100                 105                 110

Gln Ala Pro Lys
        115

<210> SEQ ID NO 75
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 75

Ala Asp Asn Arg Phe Asn Asp Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

-continued

```
Ser Leu Arg Asp Asp Pro Ser Val Ser Arg Glu Ile Leu Ala Glu Ala
         35                  40                  45
Arg Arg Leu Asn Asp Ala Gln Ala Pro Arg Ala Asp Asn Arg Phe Asn
     50                  55                  60
Asp Glu Gln Gln Asn Ala Phe Tyr Glu Ile Leu His Leu Pro Asn Leu
 65                  70                  75                  80
Thr Glu Glu Gln Arg Asn Ala Phe Ile Gln Ser Leu Arg Asp Asp Pro
                 85                  90                  95
Ser Val Ser Arg Glu Ile Leu Ala Glu Ala Arg Arg Leu Asn Asp Ala
            100                 105                 110
Gln Ala Pro Lys
        115
```

<210> SEQ ID NO 76
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 76
cttcatccaa gagttgcgcg ac    22

<210> SEQ ID NO 77
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 77
gtcgcgcaac tcttggatga ag    22

<210> SEQ ID NO 78
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 78
cttcatccaa ctgttgcgcg ac    22

<210> SEQ ID NO 79
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 79
gtcgcgcaac agttggatga ag    22

<210> SEQ ID NO 80
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 80
gcttgcgcat cgatccttca g    21

```
<210> SEQ ID NO 81
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 81
ctgaaggatc gatgcgcaag c                                        21

<210> SEQ ID NO 82
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 82
ccttcatcca acagttgcgc gacg                                     24

<210> SEQ ID NO 83
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 83
cgtcgcgcaa ctgttggatg aagg                                     24

<210> SEQ ID NO 84
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 84
ccttcatcca acatttgcac gacg                                     24

<210> SEQ ID NO 85
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 85
cgtcgtgcaa atgttggatg aagg                                     24

<210> SEQ ID NO 86
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 86
ccttcatcca acgtttgcac gacg                                     24

<210> SEQ ID NO 87
<211> LENGTH: 24
<212> TYPE: DNA
<213> ORGANISM: Artificial Sequence
<220> FEATURE:
<223> OTHER INFORMATION: synthetic oligonucleotide
```

<400> SEQUENCE: 87
cgtcgtgcaa acgttggatg aagg 24

<210> SEQ ID NO 88
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 88

```
Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Glu Leu Arg Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Glu Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Lys
        115
```

<210> SEQ ID NO 89
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 89

```
Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Leu Leu Arg Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Leu Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Lys
        115
```

<210> SEQ ID NO 90
<211> LENGTH: 116
<212> TYPE: PRT
<213> ORGANISM: Artificial Sequence
<220> FEATURE:
<223> OTHER INFORMATION: SpA C domain mutant

<400> SEQUENCE: 90

```
Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Arg Ile Asp Pro Ser Val Ser Arg Glu Ile Leu Ala Glu Ala
            35                  40                  45

Arg Arg Leu Asn Asp Ala Gln Ala Pro Arg Ala Asp Asn Arg Phe Asn
        50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Ile Asp Pro
                85                  90                  95

Ser Val Ser Arg Glu Ile Leu Ala Glu Ala Arg Arg Leu Asn Asp Ala
            100                 105                 110

Gln Ala Pro Lys
            115
```

<210> SEQ ID NO 91
<211> LENGTH: 232
<212> TYPE: PRT
<213> ORGANISM: Artificial Sequence
<220> FEATURE:
<223> OTHER INFORMATION: SpA C domain mutant

<400> SEQUENCE: 91

```
Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
                20                  25                  30

Gln Leu Arg Asp Asp Pro Ser Val Ser Arg Glu Ile Leu Ala Glu Ala
            35                  40                  45

Gln Arg Leu Asn Asp Ala Gln Ala Pro Arg Ala Asp Asn Arg Phe Asn
        50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Gln Leu Arg Asp Asp Pro
                85                  90                  95

Ser Val Ser Arg Glu Ile Leu Ala Glu Ala Gln Arg Leu Asn Asp Ala
            100                 105                 110

Gln Ala Pro Arg Ala Asp Asn Arg Phe Asn Arg Glu Gln Gln Asn Ala
        115                 120                 125

Phe Tyr Glu Ile Leu His Leu Pro Asn Leu Thr Glu Glu Gln Arg Asn
    130                 135                 140

Ala Phe Ile Gln Gln Leu Arg Asp Asp Pro Ser Val Ser Arg Glu Ile
145                 150                 155                 160

Leu Ala Glu Ala Gln Arg Leu Asn Asp Ala Gln Ala Pro Arg Ala Asp
                165                 170                 175

Asn Arg Phe Asn Arg Glu Gln Gln Asn Ala Phe Tyr Glu Ile Leu His
            180                 185                 190

Leu Pro Asn Leu Thr Glu Glu Gln Arg Asn Ala Phe Ile Gln Gln Leu
        195                 200                 205

Arg Asp Asp Pro Ser Val Ser Arg Glu Ile Leu Ala Glu Ala Gln Arg
    210                 215                 220
```

-continued

Leu Asn Asp Ala Gln Ala Pro Lys
225                 230

<210> SEQ ID NO 92
<211> LENGTH: 232
<212> TYPE: PRT
<213> ORGANISM: Artificial Sequence
<220> FEATURE:
<223> OTHER INFORMATION: SpA C domain mutant

<400> SEQUENCE: 92

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

His Leu His Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln His Leu His Asp Asp Pro
                85                  90                  95

Ser Val Ser Arg Glu Ile Leu Ala Glu Ala Arg Arg Leu Asn Asp Ala
            100                 105                 110

Gln Ala Pro Arg Ala Asp Asn Arg Phe Asn Arg Glu Gln Gln Asn Ala
        115                 120                 125

Phe Tyr Glu Ile Leu His Leu Pro Asn Leu Thr Glu Glu Gln Arg Asn
    130                 135                 140

Ala Phe Ile Gln His Leu His Asp Asp Pro Ser Val Ser Arg Glu Ile
145                 150                 155                 160

Leu Ala Glu Ala Arg Arg Leu Asn Asp Ala Gln Ala Pro Arg Ala Asp
                165                 170                 175

Asn Arg Phe Asn Arg Glu Gln Gln Asn Ala Phe Tyr Glu Ile Leu His
            180                 185                 190

Leu Pro Asn Leu Thr Glu Glu Gln Arg Asn Ala Phe Ile Gln His Leu
        195                 200                 205

His Asp Asp Pro Ser Val Ser Arg Glu Ile Leu Ala Glu Ala Arg Arg
    210                 215                 220

Leu Asn Asp Ala Gln Ala Pro Lys
225                 230

<210> SEQ ID NO 93
<211> LENGTH: 232
<212> TYPE: PRT
<213> ORGANISM: Artificial Sequence
<220> FEATURE:
<223> OTHER INFORMATION: SpA C domain mutant

<400> SEQUENCE: 93

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Arg Leu His Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

```
Arg Glu Gln Gln Asn Ala Phe Tyr Glu Ile Leu His Leu Pro Asn Leu
 65                  70                  75                  80

Thr Glu Glu Gln Arg Asn Ala Phe Ile Gln Arg Leu His Asp Asp Pro
                 85                  90                  95

Ser Val Ser Arg Glu Ile Leu Ala Glu Ala Arg Arg Leu Asn Asp Ala
            100                 105                 110

Gln Ala Pro Arg Ala Asp Asn Arg Phe Asn Arg Glu Gln Gln Asn Ala
        115                 120                 125

Phe Tyr Glu Ile Leu His Leu Pro Asn Leu Thr Glu Glu Gln Arg Asn
130                 135                 140

Ala Phe Ile Gln Arg Leu His Asp Asp Pro Ser Val Ser Arg Glu Ile
145                 150                 155                 160

Leu Ala Glu Ala Arg Arg Leu Asn Asp Ala Gln Ala Pro Arg Ala Asp
                165                 170                 175

Asn Arg Phe Asn Arg Glu Gln Gln Asn Ala Phe Tyr Glu Ile Leu His
            180                 185                 190

Leu Pro Asn Leu Thr Glu Glu Gln Arg Asn Ala Phe Ile Gln Arg Leu
        195                 200                 205

His Asp Asp Pro Ser Val Ser Arg Glu Ile Leu Ala Glu Ala Arg Arg
    210                 215                 220

Leu Asn Asp Ala Gln Ala Pro Lys
225                 230

<210> SEQ ID NO 94
<211> LENGTH: 174
<212> TYPE: PRT
<213> ORGANISM: Artificial Sequence
<220> FEATURE:
<223> OTHER INFORMATION: SpA C domain mutant

<400> SEQUENCE: 94

Ala Asp Asn Arg Phe Asn Arg Glu Gln Gln Asn Ala Phe Tyr Glu Ile
  1               5                  10                  15

Leu His Leu Pro Asn Leu Thr Glu Glu Gln Arg Asn Ala Phe Ile Gln
                 20                  25                  30

Leu Leu Arg Asp Asp Pro Ser Val Ser Arg Glu Ile Leu Ala Glu Ala
             35                  40                  45

Arg Arg Leu Asn Asp Ala Gln Ala Pro Arg Ala Asp Asn Arg Phe Asn
 50                  55                  60

Arg Glu Gln Gln Asn Ala Phe Tyr Glu Ile Leu His Leu Pro Asn Leu
 65                  70                  75                  80

Thr Glu Glu Gln Arg Asn Ala Phe Ile Gln Leu Leu Arg Asp Asp Pro
                 85                  90                  95

Ser Val Ser Arg Glu Ile Leu Ala Glu Ala Arg Arg Leu Asn Asp Ala
            100                 105                 110

Gln Ala Pro Arg Ala Asp Asn Arg Phe Asn Arg Glu Gln Gln Asn Ala
        115                 120                 125

Phe Tyr Glu Ile Leu His Leu Pro Asn Leu Thr Glu Glu Gln Arg Asn
130                 135                 140

Ala Phe Ile Gln Leu Leu Arg Asp Asp Pro Ser Val Ser Arg Glu Ile
145                 150                 155                 160

Leu Ala Glu Ala Arg Arg Leu Asn Asp Ala Gln Ala Pro Lys
                165                 170

<210> SEQ ID NO 95
```

<210> SEQ ID NO 95 (implied continuation)
<211> LENGTH: 525
<212> TYPE: DNA
<213> ORGANISM: Artificial Sequence
<220> FEATURE:
<223> OTHER INFORMATION: Code DNA

<400> SEQUENCE: 95

```
gcagacaacc gtttcaatcg cgaacagcaa aacgcgtttt atgaaattct gcatcttcca      60
aacttgacag aggaacaacg caatgctttc atccaactgc tgcgtgatga tccgagcgtt     120
tctcgtgaaa tcttggctga agcacgtcgc ctgaacgacg ctcaagctcc aaaagcggat     180
aaccgtttta accgtgaaca acaaaatgct ttctacgaga tcttgcacct tccgaacctg     240
actgaagaac aacgtaacgc atttattcag ttgttgcgtg atgacccatc cgtaagccgc     300
gagatcctgg cagaagctcg ccgcttgaat gatgcacaag ctccaaaagc agacaaccgc     360
tttaaccgcg aacaacaaaa tgcattctac gaaatcttgc accttcctaa cctgactgag     420
gagcaacgca atgctttcat ccaattgctt cgcgatgatc caagcgtaag ccgtgaaatt     480
ttggctgaag ctcgtcgtct gaacgatgca caagctccaa aataa                    525
```

<210> SEQ ID NO 96
<211> LENGTH: 174
<212> TYPE: PRT
<213> ORGANISM: Artificial Sequence
<220> FEATURE:
<223> OTHER INFORMATION: SpA C domain mutant

<400> SEQUENCE: 96

```
Ala Asp Asn Arg Phe Asn Arg Glu Gln Gln Asn Ala Phe Tyr Glu Ile
1               5                   10                  15
Leu His Leu Pro Asn Leu Thr Glu Glu Gln Arg Asn Ala Phe Ile Gln
            20                  25                  30
Leu Leu Arg Asp Asp Pro Ser Val Ser Arg Glu Ile Leu Ala Glu Ala
        35                  40                  45
Arg Arg Leu Asn Asp Ala Gln Ala Pro Lys Ala Asp Asn Arg Phe Asn
    50                  55                  60
Arg Glu Gln Gln Asn Ala Phe Tyr Glu Ile Leu His Leu Pro Asn Leu
65                  70                  75                  80
Thr Glu Glu Gln Arg Asn Ala Phe Ile Gln Leu Leu Arg Asp Asp Pro
                85                  90                  95
Ser Val Ser Arg Glu Ile Leu Ala Glu Ala Arg Arg Leu Asn Asp Ala
            100                 105                 110
Gln Ala Pro Lys Ala Asp Asn Arg Phe Asn Arg Glu Gln Gln Asn Ala
        115                 120                 125
Phe Tyr Glu Ile Leu His Leu Pro Asn Leu Thr Glu Glu Gln Arg Asn
    130                 135                 140
Ala Phe Ile Gln Leu Leu Arg Asp Asp Pro Ser Val Ser Arg Glu Ile
145                 150                 155                 160
Leu Ala Glu Ala Arg Arg Leu Asn Asp Ala Gln Ala Pro Lys
                165                 170
```

<210> SEQ ID NO 97
<211> LENGTH: 525
<212> TYPE: DNA
<213> ORGANISM: Artificial Sequence
<220> FEATURE:
<223> OTHER INFORMATION: Code DNA

<400> SEQUENCE: 97

```
gcagacaacc gtttcaatcg cgaacagcaa aacgcgtttt atgaaattct gcatcttcca         60
aacttgacag aggaacaacg caatgctttc atccaactgc tgcgtgatga tccgagcgtt        120
tctcgtgaaa tcttggctga agcacgtcgc ctgaacgacg ctcaagctcc acgcgcggat        180
aaccgtttta accgtgaaca acaaaatgct ttctacgaga tcttgcacct tccgaacctg        240
actgaagaac aacgtaacgc atttattcag ttgttgcgtg atgacccatc cgtaagccgc        300
gagatcctgg cagaagctcg ccgcttgaat gatgcacaag ctccacgcgc agacaaccgc        360
tttaaccgcg aacaacaaaa tgcattctac gaaatcttgc accttcctaa cctgactgag        420
gagcaacgca atgctttcat ccaattgctt cgcgatgatc caagcgtaag ccgtgaaatt        480
ttggctgaag ctcgtcgtct gaacgatgca caagctccaa aataa                       525
```

PROTEIN FOR AFFINITY-SEPARATION MATRIX

CROSS REFERENCE TO RELATED APPLICATIONS

This application is a National Phase filing under 35 U.S.C. § 371 of PCT/JP2012/057824 filed on Mar. 26, 2012; and this application claims priority to Application No. 2011-068498 filed in Japan on Mar. 25, 2011, under 35 U.S.C. § 119; the entire contents of all are hereby incorporated by reference.

TECHNICAL FIELD

The present invention relates to proteins capable of specifically binding to a target substance, ligand affinity separation matrices to which the proteins capable of specifically binding to a target substance are immobilized, and separation/purification methods using the matrices.

BACKGROUND ART

One important ability of proteins is to specifically bind to a specific molecule. Due to this ability, some proteins play important functions in immunoreactions and signal transmission in vivo. This ability has been the subject of intense research to develop techniques for separation and purification of useful substances using this ability. One example of such techniques already used in industrial applications is Protein A affinity separation matrices that allow for purification (capture) of high purity antibody drugs from animal cell cultures at one time.

Antibody drugs developed so far are generally monoclonal antibodies. These antibodies are mass-produced by recombinant cell-culture technology or the like. The term "monoclonal antibodies" refers to antibodies produced by clones of a single antibody-producing cell. Almost all antibody drugs currently available on the market are classified into immunoglobulin G (IgG) subclasses based on their molecular structures. Protein A is a cell wall protein produced by the gram-positive bacterium *Staphylococcus aureus*, and contains a signal sequence S, five immunoglobulin-binding domains (E domain, D domain, A domain, B domain, and C domain), and a cell wall-anchoring domain known as XM region (Non Patent Literature 1). In the initial purification step (capture step) in the process of antibody drug manufacture, affinity chromatography columns where Protein A is immobilized as a ligand on a water-insoluble carrier are commonly used (Non Patent Literatures 1 to 3).

Various techniques for improving the performance of Protein A columns have been developed. Various technological developments in ligands have also been made. Initially, wild-type Protein A has been used as a ligand, and currently, Protein A variants recombinantly produced by protein engineering are used as ligands in many techniques for improving the column performance. Notably, some of the Protein A engineering techniques proposed so far aim to provide Protein A ligands that can be immobilized on a water-insoluble carrier via a specific bond.

Recombinant Protein A with an additional Cys (cysteine) residue can be site-specifically immobilized on a carrier through the Cys residue (Patent Literature 1). Recombinant Protein A obtained by mutating Protein A such that the ratio between the number of Lys (lysine) residues in the antibody binding surface and the number of Lys (lysine) residues in the non-antibody binding surface of Protein A is changed can be immobilized on a carrier through multiple residues while mildly controlling the orientation of this ligand (Patent Literature 2). Recombinant Protein A with deletion of all Lys or Cys residues in the amino acid sequence can be immobilized on a carrier through its N terminal (through the α-amino group) or C terminal (through a special tag) (Patent Literatures 3 and 4). Thus, developments in technology for immobilizing a protein ligand to an affinity separation matrix are mainly based on techniques relating to Protein A columns that are required to have high performance because of their high industrial importance.

CITATION LIST

Patent Literature

Patent Literature 1: WO 1997/017361
Patent Literature 2: JP 2007-252368 A
Patent Literature 3: JP 2008-115151 A
Patent Literature 4: JP 2008-266219 A

Non Patent Literature

Non Patent Literature 1: Hober S. et al., "J. Chromatogr. B" 2007, Vol. 848, 40-47
Non Patent Literature 2: Low D. et al., "J. Chromatogr. B", 2007, Vol. 848, 48-63
Non Patent Literature 3: Roque A. C. A. et al., "J. Chromatogr. A", 2007, Vol. 1160, 44-55

SUMMARY OF INVENTION

Technical Problem

An object of the present invention is to provide a technique for creating novel engineered protein ligands that confer the optimum binding capacity and binding efficiency to a target molecule.

Solution to Problem

In order to achieve the object, the present inventors molecularly designed a large number of recombinant variants of Protein A, which is the most typical affinity purification protein ligand, created these variants by protein engineering techniques and genetic engineering techniques, and compared the physical properties of these variants and the performance of antibody affinity separation matrices in which these variants are immobilized on a water-insoluble carrier. The comparison revealed that a variant with deletion of all the Lys residues of Protein A and addition of a Lys residue to a terminal can be efficiently immobilized on a carrier through the Lys residue (through its side chain ε-amino group), and confer the optimum binding capacity and binding efficiency to a target molecule. Accordingly, the present inventors completed the present invention.

Specifically, the present invention provides a protein containing an amino acid sequence obtained by introducing, into an amino acid sequence derived from at least one domain selected from E, D, A, B and C domains of Protein A, amino acid substitutions for all Lys (lysine) residues, and adding Lys to a terminal.

Preferably, the amino acid sequence before the introduction of substitutions includes amino acid sequences derived from two or more of the Protein A domains.

Preferably, the amino acid sequence before the introduction of substitutions includes at least one of amino acid sequences of SEQ ID No:1 to 5 or at least one of amino acid sequences respectively obtained by mutating the amino acid sequences of SEQ ID No:1 to 5 by introducing at least one of the following mutations (1) to (4):

(1) substitution of Ala, Val, Leu, Ile, Phe, Tyr, Trp, Thr, Ser, Asp, Glu, Arg, His, or Met for an amino acid residue corresponding to position 29 of the C domain;

(2) substitution of Leu, Ile, Phe, Tyr, Trp, Thr, Asp, Glu, Asn, Gln, Arg, His, or Met for an amino acid residue corresponding to position 33 of the C domain;

(3) substitution of Leu, Ile, Phe, Tyr, Trp, Glu, Arg, His, or Met for an amino acid residue corresponding to position 36 of the C domain; and (4) substitution of Leu, Ile, Phe, Tyr, Trp, Glu, Arg, His, or Met for an amino acid residue corresponding to position 37 of the C domain.

Preferably, not less than half of the amino acid substitutions for all the Lys residues are substitutions of Arg, and more preferably, all the substitutions are substitutions of Arg.

Preferably, 90% or more of Gln-9, Gln-10, Phe-13, Tyr-14, Leu-17, Pro-20, Asn-21, Leu-22, Gln-26, Arg-27, Phe-30, Ile-31, Leu-34, Pro-38, Ser-39, Leu-45, Leu-51, Asn-52, Gln-55, and Pro-57 (the residue numbers are corresponding residue numbers of the C domain) are conserved in the protein, and the protein has at least 80% sequence identity to the amino acid sequence before the introduction of substitutions.

Preferably, two or more of the domains of the Protein A are linked to one another through a linker. Preferably, the linker contains Lys.

The present invention also relates to a DNA encoding the protein, and a vector containing the DNA, and a transformant obtainable by transforming the vector into a host cell.

The present invention also relates to a method for producing the protein using either a cell-free protein synthesis system incorporating the DNA or the transformant.

The present invention further relates to an affinity separation matrix containing: the protein as an affinity ligand; and a carrier made of a water-insoluble base material on which the protein is immobilized.

The affinity separation matrix preferably binds to a protein containing an Fc region of an immunoglobulin, and the protein containing an Fc region of an immunoglobulin is preferably an immunoglobulin G or an immunoglobulin G derivative.

The present invention further relates to a method for preparing the affinity separation matrix, the method including immobilizing the protein as an affinity ligand on a carrier made of a water-insoluble material.

The present invention further relates to a method for purifying a protein containing an Fc region of an immunoglobulin, the method including adsorbing the protein containing an Fc region of an immunoglobulin to an affinity separation matrix.

Advantageous Effects of Invention

Affinity separation matrices that include a novel engineered protein ligand of the present invention, and a water-insoluble carrier on which the protein is immobilized through a Lys (lysine) residue among amino acid residues in the protein by reductive amination or the like show high binding capacity to a target molecule even when the immobilized amount of the ligand is small.

The ε-amino group of the side chain of Lys is a primary amino group that is very useful for immobilization of ligands, and techniques for improving the binding capacity to a target molecule which make use of this immobilization manner are practically valuable. Additionally, these techniques are very effective in reducing the cost (the immobilized amount of ligands) because they allow proteins, the production of which costs so much, to function at their highest performance. Intense efforts are also underway to develop base materials for affinity separation matrices incorporating Protein A as a ligand, and this particularly increases the practical usefulness of these techniques.

Proteins of the present invention are engineered proteins obtainable by substitutions for all the Lys residues in a sequence of Protein A, and addition of Lys to a terminal. Actually, it is difficult for such proteins to maintain the functions of the original proteins before engineering, in particular the affinity to a target molecule, which is a desired function.

Additionally, proteins with these mutations, when immobilized on a carrier through the terminal Lys, may not be in the same desired orientation as the original proteins. It is difficult to estimate the entire conformation of the proteins of the present invention which are significantly engineered by substitutions for all the Lys residues, in particular, that of multi-domain proteins among them. In fact, the present inventors obtained experimental data indicating the likelihood that the entire conformation of multi-domain proteins of the present invention is changed.

Although the proteins of the present invention are significantly engineered by substitutions for all the Lys residues that constitute 10% or more of the original proteins, and addition of Lys to a terminal, the proteins surprisingly maintain the original affinity to a target molecule, and are immobilized in use to confer improved binding capacity to the target molecule.

BRIEF DESCRIPTION OF DRAWINGS

FIG. 3 shows an SDS-PAGE profile of a polypeptide after an alkali treatment (0, 4, and 24 hours) in Example 12.

DESCRIPTION OF EMBODIMENTS

Figures 1, 2:
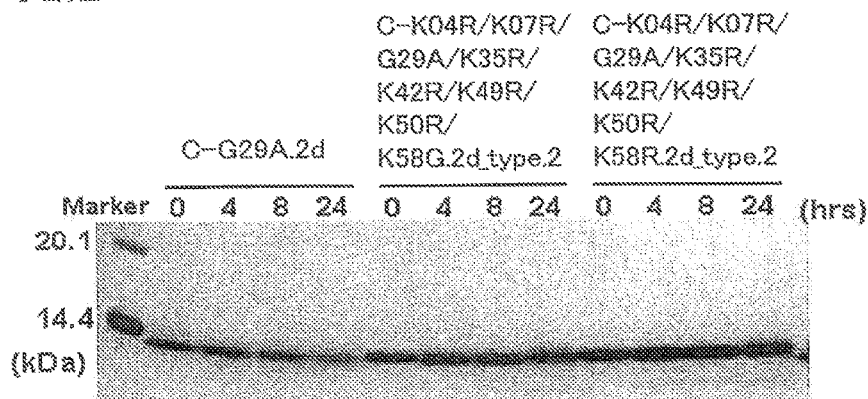
FIG. 1 is a table for comparison of the sequences of E (SEQ ID NO. 1), D (SEQ ID NO. 2), A (SEQ ID NO. 3), B (SEQ ID NO. 4) and C (SEQ ID NO. 5) domains of staphylococcal Protein A; the SEQ ID Nos: 1-5 correspond to the sequences in FIG. 1 (i.e. sequences E, D, A, B and C, respectively)
FIG. 2 shows an SDS-PAGE profile of a polypeptide after an alkali treatment (0, 4, 8, and 24 hours) in Example 8.

Amino acid substitutions are each represented herein by an amino acid residue of the wild-type or non-mutated type, followed by the position number of the substitution, followed by an amino acid residue introduced by the substitution. For example, a substitution of Ala for Gly at position 29 is represented by G29A.

The term "protein" herein is intended to include any molecules of polypeptide structure and therefore include fragmented polypeptide chains and polypeptide chains linked through peptide bonds as well.

The term "domain" generally refers to a higher-order protein structural unit which consists of several tens or hundreds of amino acid residues, and is able to fulfill a certain physicochemical or biochemical function. The term "domain" herein especially refers to domains capable of binding to proteins containing an Fc region of an immunoglobulin, and specific examples include any of E, D, A, B, and C domains of staphylococcal Protein A, B1 and B2 domains of streptococcal Protein G, and B1 to B4 domains of peptostreptococcal Protein L (Kihilberg B. M. et al., "J. Biol. Chem." 1992, Vol. 267, 25583-25588). The C1 and C2 domains of Protein G are also referred to as B1 and B2 domains or G1 and G2 domains, respectively, in some literatures. Among these, E, D, A, B, and C domains of staphylococcal Protein A shown as SEQ ID Nos:1 to 5 and amino acid sequences derived from these domains are preferable. These domains can be aligned as shown in FIG. 1. For example, the amino acid residue at position 31 of the C domain corresponds to position 31 of the A and B domain, position 29 of the E domain, and position 34 of the D domain.

The E, D, A, B and C domains of Protein A are immunoglobulin-binding proteins having an ability to bind to a region other than complementarity determining regions (CDRs) of immunoglobulins. All the domains are capable of binding to the Fc and Fab regions of immunoglobulins and particularly the Fv region in the Fab region. In general, the domains of Protein A more strongly bind to the Fc region than to the Fab (Fv) region (Non Patent Literature 3). Thus, the "affinity for an immunoglobulin" of Protein A and the domains essentially refers to the affinity for the Fc region, and the degree of affinity for an immunoglobulin does not largely change when only the binding ability to the Fab region is changed.

Protein A is a protein containing five immunoglobulin-binding domains, in other words, five immunoglobulin-binding proteins. The immunoglobulin-binding proteins of the present invention are preferably proteins likewise containing multiple domains connected together. In one embodiment, the lower limit of the number of connected monomeric proteins (monomeric domains) is 2 or more, preferably 3 or more, more preferably 4 or more, and still more preferably 5 or more, and the upper limit thereof is 20 or less, preferably 10 or less, more preferably 8 or less, and still more preferably 6 or less. These proteins may be homopolymers (e.g. homodimers, homotrimers) consisting of connected immunoglobulin-binding proteins of a single type and additional Lys residue(s) at a terminal, or may be heteropolymers (e.g. heterodimer, heterotrimer) consisting of connected immunoglobulin-binding proteins of different types and additional Lys residue(s) at a terminal.

Such monomeric proteins may be connected without any linker amino acid residues or through one or more amino acid residues, but the connection is not limited only to these manners. The number of linker amino acid residues is not limited at all. Preferably, the monomeric proteins are connected without destabilizing the three-dimensional structure of these proteins.

The term "linker" herein means a linker between domains, and refers to a sequence connecting monomeric proteins (monomeric domains), in other words, a region in which a C terminal region of a domain sequence on the N-terminal side and an N terminal region of a domain sequence on the C-terminal side are connected. In the case of a protein containing N domains connected in tandem, the number of linkers in the protein is N−1. Namely, the "linker" herein refers to a region consisting of at least two amino acid residues of connected domains including the C-terminal amino acid residue of the domain on the N-terminal side and the N-terminal amino acid residue of the domain on the C-terminal side.

Sequences devoid of specific secondary structures or bordering sequences at the N or C terminal of domains can function as linkers. Specifically, in the immunoglobulin G-binding domains of Protein A, for example, amino acid residues at the N terminal corresponding to positions 1 to 6 of the C domain, preferably positions 1 to 5, more preferably positions 1 to 4, still more preferably positions 1 to 3, particularly preferably positions 1 to 2, function as a linker, and at least the N-terminal amino acid residue functions as a linker. It should be noted that although the E and D domains differ from the C domain in the full length, the amino acid residues in these domains corresponding to the above-mentioned amino acid residues of the C domain function as a linker. Likewise, in the immunoglobulin G-binding domains of Protein A, amino acid residues at the C terminal corresponding to positions 55 to 58 of the C domain, preferably positions 56 to 58, more preferably positions 57 to 58, function as a linker. Thus, at least the C-terminal amino acid residue at position 58 functions as a linker.

One embodiment provides fusion proteins in which an immunoglobulin G-binding protein of the present invention or a multimeric protein consisting of a dimer or higher-order multimer of immunoglobulin G-binding protein(s) of the present invention is fused with another proteinic component having a different function. Examples of the fusion proteins include, but are not limited to, fusion proteins with albumin and GST (glutathione S-transferase). Additionally, fusion proteins with a nucleic acid (e.g. a DNA aptamer), a drug (e.g. an antibiotic) or a polymer (e.g. PEG (polyethylene glycol)) are also encompassed within the scope of the present invention, provided that they take advantage of the effects of the proteins of the present invention.

The expression "protein having an amino acid sequence derived from at least one domain" herein refers to proteins before the introduction of mutations. The amino acid sequences of proteins before the introduction of mutations are not limited only to the wild-type amino acid sequences of the E, D, A, B and C domains of Protein A, and are intended to also include amino acid sequences partially engineered by substitution, insertion, deletion and chemical modification of amino acid residue(s), provided that they encode proteins having a binding ability to the Fc region. For example, the Z domain, which is obtained by introducing the A1V and G29A mutations into the B domain, is regarded as a sequence derived from the B domain, and proteins obtained by introducing the mutations according to the present invention to the Z domain are also encompassed within the scope of the proteins of the present invention.

The proteins of the present invention are characterized by Lys residue(s) at a terminal. The lower limit of the number of additional Lys residues is 1 or more, preferably 2 or more, and more preferably 3 or more, and the upper limit thereof is 10 or less, and preferably 5 or less. In the case where multiple Lys residues are present, the lysine residues may not be consecutive (next to one another). The number of terminal amino acid residues including lysine residue(s) is not limited at all, and the terminal sequence may consist of only one lysine residue. The lower limit of the number of terminal amino acid residues including lysine residue(s) is 1 or more, preferably 2 or more, and more preferably 3 or more, and the upper limit thereof is 20 or less, preferably 10 or less, and more preferably 5 or less. The expression "addition to a terminal" basically means addition to the N or C terminal of an amino acid sequence.

The C terminals of the A to E domains are Lys. In the case of single-domain proteins, only Lys-58 (the residue number is a corresponding residue number of the C domain) may be conserved without mutation at this residue. In the case of multi-domain proteins, only Lys-58 (the residue number is a corresponding residue number of the C domain) of each domain may be conserved without mutation at this residue. For example, in the case of a multi-domain protein containing domains without Lys at the C terminal, the ligand should contain Lys-58 in the C-terminal domain. Such ligands may contain one or more Lys residues in linker region(s) outside the C-terminal domain. Or, the linker may contain only Lys-58 in the C-terminal domain without Lys in the linker region(s). Practically, the amino acid sequences of all of these cases are identical to "amino acid sequence obtained by introducing amino acid substitutions for all Lys (lysine) residues, and adding Lys to a terminal".

The amino acid sequences derived from the domains are preferably amino acid sequences respectively obtained by mutating the amino acid sequences of SEQ ID No:1 to 5 by introducing at least one of the following mutations (1) to (4):

(1) substitution of Ala, Val, Leu, Ile, Phe, Tyr, Trp, Thr, Ser, Asp, Glu, Arg, His, or Met for an amino acid residue corresponding to position 29 of the C domain;

(2) substitution of Leu, Ile, Phe, Tyr, Trp, Thr, Asp, Glu, Asn, Gln, Arg, His, or Met for an amino acid residue corresponding to position 33 of the C domain;

(3) substitution of Leu, Ile, Phe, Tyr, Trp, Glu, Arg, His, or Met for an amino acid residue corresponding to position 36 of the C domain; and (4) substitution of Leu, Ile, Phe, Tyr, Trp, Glu, Arg, His, or Met for an amino acid residue corresponding to position 37 of the C domain.

More preferred are amino acid sequences engineered by at least one of the following amino acid residue substitutions (1) to (4):

(1) substitution of Ala, Glu, or Arg for an amino acid residue corresponding to position 29 of the C domain;

(2) substitution of Leu, Thr, Glu, Gln, Arg, or His for an amino acid residue corresponding to position 33 of the C domain;

(3) substitution of Ile or Arg for an amino acid residue corresponding to position 36 of the C domain; and (4) substitution of Leu, Ile, Glu, Arg, or His for an amino acid residue corresponding to position 37 of the C domain.

The term "all Lys (lysine) residues" refers to 6 Lys residues of the E, D, A, and B domains of Protein A corresponding to positions 4, 7, 35, 49, 50, and 58 of the C domain. For the C domain of Protein A, the term refers to 7 Lys residues at positions 4, 7, 35, 42, 49, 50, and 58. It should be noted that in the case where amino acid sequences that already contain deletion of amino acid residues, for example, at positions 1 to 4 are used as the amino acid sequences before the introduction of mutations, these numbers may not apply to these amino acid sequences.

Amino acids substituted for the Lys sites are not limited at all, and may be natural amino acids, non-proteinogenic amino acids, or non-natural amino acids. Particularly, from the viewpoint of production by genetic engineering, natural amino acids are preferably used. Amino acids with a side chain having a functional group that is reactive in a coupling reaction for immobilization, such as cysteine (Cys), which has a thiol group (—SH) in the side chain, are not suited for the substitutions.

The following shows specific examples of amino acid substitution mutations.

(1) Substitution of Arg, Gln, or Asn for Lys in the D, B, and C domains corresponding to position 4 of the C domain. Arg is preferable.

(2) Substitution of Asp, Arg, or Glu for Lys in the D, A, B, and C domains corresponding to position 7 of the C domain. Arg is preferable.

(3) Substitution of Arg, Ile, or His for Lys in the E, D, A, B, and C domains corresponding to position 35 of the C domain. Arg or His is preferable.

(4) Substitution of Arg for Lys at position 42 of the C domain.

(5) Substitution of Arg or Gln for Lys in the D, A, B, and C domains corresponding to position 49 of the C domain.

(6) Substitution of Arg or His for Lys in the E, D, A, B, and C domains corresponding to position 50 of the C domain. Arg is preferable.

(7) Substitution of Arg or Gly for Lys in the E, D, A, B, and C domains corresponding to position 58 of the C domain. Arg is preferable. It should be noted that in the case where this amino acid residue is located at (or near) the C terminal of a ligand, this residue may be conserved without mutation at this site, as described above.

Additionally, not less than half of the amino acids substituted for the Lys sites are preferably arginine (Arg), and more preferably all of them are Arg. This is because Arg and Lys are both basic amino acids having similar properties, and substitution of Arg for Lys relatively does not affect on the properties of the whole protein.

Further, one embodiment provides affinity ligands that show high chemical stability under alkali conditions. In this embodiment, amino acid sequences derived from the C domain of SEQ ID No:5 are preferably selected as the amino acid sequences before the introduction of mutations of the present invention. More preferably, amino acid sequences derived from the C domain of SEQ ID No:5 where the amino acid residue corresponding to position 29 is any of Ala, Arg, Glu, Ile, Leu, Met, Phe, Trp, and Tyr are selected as the amino acid sequences before the introduction of mutations of the present invention. Preferably, not less than half of the amino acids substituted for the Lys residues are preferably arginine (Arg), and more preferably all of them are Arg. In the case where all the substitutions are substitutions of Arg, the chemical stability under alkali conditions is improved compared to that before the introduction of these mutations.

The chemical stability under alkali conditions can be determined as a measure of the binding activity to an immunoglobulin, or as a measure of the stability of a polypeptide itself. In the case where the chemical stability under alkali conditions is determined as a measure of the stability of a polypeptide itself, it can be evaluated, for example, by comparing electrophoresis bands of the polypeptide before and after an alkali treatment. Specifically, comparison of the chemical stability can be performed by analyzing the polypeptide before and after an alkali treatment by general SDS-PAGE, and analyzing bands with a densitometry for intensity. When evaluated by the analysis for band intensity using a densitometry, the polypeptides of the present invention preferably have a chemical stability, as measured after being left in a 0.5 M sodium hydroxide aqueous solution at 25° C. for 24 hours, of not less than 50% of that measured before this treatment, more preferably not less than 60%, still more preferably not less than 70%, and most preferably not less than 80%.

Proteins with very high sequence identity to the variants obtainable by the present invention are also included in the scope of the present invention. In the case where the sequence identity is evaluated based on the following 20 amino acid residues which are conserved in all the domains, preferably at least 90%, more preferably at least 95%, of these amino acid residues are conserved.

Gln-9, Gln-10, Phe-13, Tyr-14, Leu-17, Pro-20, Asn-21, Leu-22, Gln-26, Arg-27, Phe-30, Ile-31, Leu-34, Pro-38,

Ser-39, Leu-45, Leu-51, Asn-52, Gln-55, Pro-57 (The residue numbers are corresponding residue numbers of the C domain.)

Additionally, when evaluated based on the entire amino acid sequence, the proteins preferably have at least 80%, more preferably at least 85%, still more preferably at least 90%, and most preferably at least 95% sequence identity to the amino acid sequences before the introduction of mutations.

The present invention also relates to DNAs having a base sequence encoding a protein produced by the above method. The DNAs may be any DNAs, the base sequences of which can be translated into amino acid sequences of the proteins described above. Such DNAs can be obtained by common known techniques, for example, using polymerase chain reaction (hereinafter, abbreviated as PCR) technology. Alternatively, the DNAs can be synthesized by known chemical synthesis techniques, or are available from DNA libraries. Codon(s) in the base sequences of these DNAs may be replaced with degenerate codon(s), in other words, their base sequences may not be completely the same as the original base sequences, provided that the translated amino acids are the same as those encoded by the original base sequences.

Site-directed mutagenesis for engineering the base sequences of the DNAs can be carried out as follows, using recombinant DNA technology, PCR technology, or the like.

Specifically, the following describes mutagenesis by recombinant DNA technology. For example, in the case where there are suitable restriction enzyme recognition sequences on both sides of a mutagenesis target site in the gene encoding a protein of the present invention, cassette mutagenesis can be used in which a region containing the mutagenesis target site is removed by cleaving these restriction enzyme recognition sequences with the restriction enzymes, and then a DNA fragment containing a mutation only at the target site, prepared by a method such as chemical synthesis, is inserted.

Site-directed mutagenesis by PCR can be accomplished by, for example, double primer mutagenesis in which PCR is carried out using a double-stranded plasmid encoding a protein as a template, and two kinds of synthetic oligo primers containing mutation, complementary to the + and − strands.

Also, a DNA encoding a multimeric protein can be produced by ligating the desired number of DNAs each encoding a monomeric protein (single domain) of the present invention in tandem. Ligation to produce a DNA encoding a multi-domain protein can be accomplished, for example, by introducing a suitable restriction enzyme recognition sequence into DNA sequences, fragmenting the DNA sequences with the restriction enzyme, and ligating the obtained double-stranded DNA fragments using a DNA ligase. Only one restriction enzyme recognition sequence may be introduced, or different restriction enzyme recognition sequences may be introduced.

The method for producing a DNA encoding a multimeric protein is not limited to this ligation method. Another candidate method for producing such a DNA is to apply the aforementioned mutagenesis techniques to, for example, a DNA encoding Protein A (for example, WO 2006/004067). If the base sequences each encoding a monomeric protein in the DNA encoding a multimeric protein are the same, homologous recombination may occur when the DNA is transformed into host cells. Therefore, the ligated DNAs each encoding a monomeric protein preferably have 90% or lower base sequence identity, and more preferably 85% or lower base sequence identity to one another.

The "vector" of the present invention refers to one containing a base sequence encoding a protein described above or a partial amino acid sequence of such a protein and a promoter that is operably ligated to the base sequence to function in host cells. Typically, these vectors can be constructed by ligating or inserting a gene encoding a protein described above to a suitable vector. The vector to which a gene is to be inserted is not limited at all, provided that it is capable of autonomous replication in host cells. As such a vector, a plasmid DNA or a phage DNA can be used. For example, in the case of using Escherichia coli host cells, examples of the vector include pQE series vectors (QIAGEN), pET series vectors (Merck), and pGEX series vectors (GE health care, Japan). Examples of plasmid vectors useful for gene expression in Brevibacillus host cells include the known Bacillus subtilis vectors pUB110, and pHY500 (JP H02-31682 A), pNY700 (JP H04-278091 A), pNU211R2L5 (JP H07-170984 A), and pHT210 (JP H06-133782 A), and the shuttle vector pNCMO2 for Escherichia coli and bacteria of Brevibacillus (JP 2002-238569 A).

The proteins of the present invention can be prepared as fusion proteins with a protein that is known to help expression of proteins or facilitate purification of proteins. Examples of such proteins include, but are not limited to, maltose-binding protein (MBP) and glutathione S-transferase (GST). Such fusion proteins can be produced using a vector in which a DNA of the present invention and a DNA encoding MBP, GST, or the like are ligated together.

The transformants of the present invention are obtainable by transfection of a recombinant vector of the present invention into a host. Examples of the method for transfecting a recombinant DNA into host cells include, but are not limited to, a method using calcium ions, an electroporation method, a spheroplast method, a lithium acetate method, an Agrobacterium infection method, a particle gun method, and a polyethylene glycol method. In order for the resulting genes to express their function in the host cells, for example, a method including incorporation of the genes obtained in the present invention into the genome (chromosome) may be used.

The host is not limited at all, and preferred examples of those suited for low-cost mass production include Escherichia coli, Bacillus subtilis and bacteria (eubacteria) of genera including Brevibacillus, Staphylococcus, Streptococcus, Streptomyces, and Corynebacterium.

The proteins of the present invention can be produced by culturing the transformants in media to produce and accumulate the proteins of the present invention in the cultured cells (including the periplasmic space thereof) or in the liquid cultures (extracellularly), and collecting the target proteins from the cultures.

Alternatively, the proteins of the present invention can be produced by culturing the transformants in media to produce and accumulate fusion proteins containing the proteins of the present invention in the cultured cells (including the periplasmic space thereof) or in the liquid cultures (extracellularly), collecting the fusion proteins from the cultures, cleaving the fusion proteins with an appropriate protease, and collecting the target proteins.

The transformants of the present invention can be cultured in media in accordance with a common method for culturing host cells. The media to be used for culturing the obtained transformants is not limited at all, provided that they allow for high-yield, high-efficiency production of the proteins. Specifically, carbon and nitrogen sources such as glucose, sucrose, glycerol, polypeptone, meat extracts, yeast extracts, and casamino acids can be used. In addition, the media may be supplemented, as required, with inorganic salts such as potassium salts, sodium salts, phosphates, magnesium salts, manganese salts, zinc salts, and iron salts. In the case of auxotrophic host cells, nutritional substances necessary for their growth are added to the media. Moreover, antibiotics such as penicillin, erythromycin, chloramphenicol, and neomycin may be optionally added.

Furthermore, any one or more of a variety of known protease inhibitors such as phenylmethane sulfonyl fluoride (PMSF), benzamidine, 4-(2-aminoethyl)-benzenesulfonyl fluoride (AEBSF), antipain, chymostatin, leupeptin, pepstatin A, phosphoramidon, aprotinin, and ethylenediaminetetraacetic acid (EDTA), and other commercially available protease inhibitors may be added at appropriate concentrations in order to inhibit degradation or molecular-size reduction of the target proteins by a host-derived protease present inside or outside the cells.

In order to assist accurate folding of the proteins of the present invention, a molecular chaperone such as GroEL/ES, Hsp70/DnaK, Hsp90 and Hsp104/ClpB may be used (for example, such a molecular chaperone can be coexpressed with a protein of the present invention or can be allowed to coexist with a protein of the present invention by combining them into a fusion protein or the like.) Further examples of techniques for accurate folding of the proteins of the present invention include, but are not limited to, addition of an additive for assisting accurate folding to the media; and culturing at low temperatures.

Examples of media for culturing transformants obtained using *Escherichia coli* host cells include LB medium (1% triptone, 0.5% yeast extract, 1% NaCl) and 2xYT medium (1.6% triptone, 1.0% yeast extract, 0.5% NaCl).

Examples of media for culturing transformants obtained using *Brevibacillus* host cells include TM medium (1% peptone, 0.5% meat extract, 0.2% yeast extract, 1% glucose, pH 7.0) and 2SL medium (4% peptone, 0.5% yeast extract, 2% glucose, pH 7.2).

The proteins of the present invention are accumulated in the cultured cells (including the periplasmic space thereof) or in the liquid cultures (extracellularly) by aerobically culturing the cells at a temperature of 15° C. to 42° C., preferably 20° C. to 37° C., for several hours to several days in an aeration-stirring condition, and then recovered. Optionally, the cells may be cultured anaerobically without aeration.

In the case where a recombinant protein is secreted, the produced recombinant protein can be recovered, after culturing the cells, by separating the cultured cells from the supernatant containing the secreted protein by a common separation method such as centrifugation and filtration.

Also, in the case where the protein is accumulated in the cultured cells (including the periplasmic space thereof), the protein accumulated in the cells can be recovered, for example, by collecting the cells from the culture liquid by centrifugation, filtration or the like, and then disrupting the cells by sonication, a French press treatment or the like, and/or adding an agent for making the protein soluble, such as a surfactant.

Purification of the proteins of the present invention can be accomplished by any one or an appropriate combination of techniques such as affinity chromatography, cation or anion exchange chromatography and gel filtration chromatography.

Examples of techniques to confirm whether a purified product is a target protein include common techniques such as SDS polyacrylamide gel electrophoresis, N-terminal amino acid sequence analysis, and Western blot analysis.

The proteins of the present invention can be produced by a cell-free protein synthesis system incorporating a DNA described above. Examples of such a cell-free protein synthesis system include synthesis systems derived from procaryotes, plant cells, and higher animal cells.

The present invention encompasses, as one embodiment, use of the proteins as affinity ligands having affinity for an immunoglobulin. The present invention further encompasses, as one embodiment, affinity separation matrices containing such a ligand as described above and a carrier made of water-insoluble base material on which the ligand is immobilized.

The term "affinity ligand" refers to a substance (functional group) that selectively captures (binds to) a target molecule in a mixture of molecules due to a specific affinity between molecules, typically, antigen-antibody binding affinity, and refers herein to a protein that specifically binds to an immunoglobulin. The term "ligand" as used alone herein is synonymous with the "affinity ligand".

The affinity for an immunoglobulin can be tested by, for example, but not limited to, a biosensor such as a Biacore system (GE health care, Japan) based on the surface plasmon resonance principle. The measurement conditions may be determined such that a binding signal emitted when Protein A binds to the Fc region of an immunoglobulin can be detected. Specifically, the affinity can be easily evaluated by measurement at a temperature of 20° C. to 40° C. (constant temperature) and a neutral pH of 6 to 8.

Examples of binding parameters include the affinity constant (KA) and the dissociation constant (KD) (Nagata et al., "Real-time analysis of biomolecular interactions", Springer-Verlag Tokyo, 1998, p. 41). The affinity constants of the proteins of the present invention for Fc can be determined with a Biacore system by adding each domain variant to a flow channel in an experimental system that includes a sensor chip with human IgG immobilized thereon, at a temperature of 25° C. and a pH of 7.4. The proteins of the present invention preferably have an affinity constant (KA) for human IgG of not less than $1 \times 10^5$ ($M^{-1}$), more preferably not less than $1 \times 10^6$ ($M^{-1}$), and still more preferably not less than $1 \times 10^7$ ($M^{-1}$).

Examples of the carrier made of a water-insoluble base material used in the present invention include inorganic carriers such as glass beads and silica gel; organic carriers such as synthetic polymers (e.g. cross-linked polyvinyl alcohol, cross-linked polyacrylate, cross-linked polyacrylamide, cross-linked polystyrene) and polysaccharides (e.g. crystalline cellulose, cross-linked cellulose, cross-linked agarose, cross-linked dextran); and composite carriers of combinations of these carriers such as organic-organic or organic-inorganic composite carriers. Examples of commercially-available products thereof include GCL2000 (porous cellulose gel), Sephacryl S-1000 (prepared by covalently cross-linking allyl dextran with methylenebisacrylamide), Toyopearl (methacrylate carrier), Sepharose CL4B (cross-linked agarose carrier) and Cellufine (cross-linked cellulose carrier). It should be noted that the carriers listed above do not limit the range of water-insoluble carriers usable in the present invention.

In view of the purpose and manner of usage of the affinity separation matrices, the water-insoluble carrier used in the present invention desirably has a large surface area, and is preferably a porous matrix having a large number of fine pores of a suitable size. The carrier may be in any form such as beads, monolith, fiber, or film (including hollow fiber), and any form can be selected appropriately.

The ligands can be immobilized on a carrier in any manner via a covalent bond through the ε-amino group of lysine residue(s) of the ligands by a known coupling method. Some of the ligand molecules may be immobilized on the carrier through the α-amino group at the N terminal, but this immobilization through the protein terminal does not adversely affect the effects of the present invention.

Examples of such a coupling method include immobilization methods including activation of the carrier by reacting the carrier with cyanogen bromide, epichlorohydrin, diglycidyl ether, tosyl chloride, tresyl chloride, hydrazine, sodium periodate, or the like (or introduction of a reactive functional group into the carrier surface), followed by a coupling reaction between the carrier and a compound to be immobilized as a ligand; and immobilization methods involving condensation and crosslinking by adding a condensation reagent such as carbodiimide or a reagent containing a plurality of functional groups in the molecule, such as glutaraldehyde, to a system containing the carrier and a compound to be immobilized as a ligand. A spacer molecule consisting of a plurality of atoms may also be introduced between the ligands and the carrier, or alternatively, the ligands may be directly immobilized on the carrier.

The affinity separation matrices of the present invention can be used to separate and purify a protein containing an Fc region of an immunoglobulin by affinity column chromatography purification techniques. The regions to which immunoglobulin-binding domains bind are loosely defined as "Fab region (in particular, Fv region)" and "Fc region", and the Fab or Fc region can be engineered (for example, by fragmenting) while maintaining the three-dimensional structure of the site to which Protein A binds by protein engineering techniques based on the three-dimensional structure of the antibody, which is already known. Accordingly, the present invention is not designed only for immunoglobulin molecules containing the intact Fab and Fc regions, and derivatives of these. Namely, the term "protein containing an Fc region of an immunoglobulin" refers to proteins containing a site derived of the Fc region to which Protein A binds, and these proteins may not contain the intact Fc region, provided that Protein A is able to bind to these proteins.

Typical examples of the protein containing an Fc region of an immunoglobulin include, but are not limited to, immunoglobulin Gs and immunoglobulin G derivatives. The term "immunoglobulin G derivatives" herein is a generic name of engineered synthetic proteins to which Protein A binds, such as chimeric immunoglobulin Gs in which domain(s) of human IgG is/are partially replaced and fused with IgG domain(s) of another species, humanized immunoglobulin Gs in which CDRs (Complementarity Determining Regions) of human IgG are replaced and fused with antibody CDRs of another species, immunoglobulin Gs whose Fc region has a molecularly engineered sugar chain, and artificial immunoglobulin Gs in which the Fv region and the Fc region of human IgG are fused.

Purification of such proteins containing an Fc region of an immunoglobulin is accomplished in accordance with an affinity column chromatography purification method using a Protein A column which is already on the market (Non Patent Literature 3). Specifically, a buffer containing a protein containing an Fc region of an immunoglobulin is neutralized and the resulting solution is run through the affinity column filled with an affinity separation matrix of the present invention so that the protein containing an Fc region of an immunoglobulin is adsorbed on the affinity separation matrix. Next, an adequate amount of a pure buffer is run through the affinity column to wash the inside of the column. At this time, the target protein containing an Fc region of an immunoglobulin remains adsorbed on the affinity separation matrix of the present invention in the column. Subsequently, an acidic buffer adjusted to an adequate pH (which may contain a substance for accelerating dissociation of the protein from the matrix) is run through the column to elute the target protein containing an Fc region of an immunoglobulin. Thus, high-level purification can be achieved.

The affinity separation matrices of the present invention can be reused through a washing process in which a pure buffer (in some cases, a solution containing an appropriate modifier or organic solvent) having an adequately strong acidity or alkalinity which does not completely impair the functions of the ligand compound and the carrier base material is run through the matrices.

The present invention further relates to proteins obtainable by a separation method using the affinity separation matrices. These proteins are preferably proteins containing an Fc region of an immunoglobulin. Proteins obtainable by using the affinity separation matrices can be obtained as high-purity, high-concentration solutions, and maintain their original activities such as ability to bind to an antigen.

EXAMPLES

The following description is offered to illustrate in more detail the present invention based on examples, but the scope of the present invention is not limited to these examples. Proteins obtained in examples are each, represented by "an alphabet indicating a domain—an introduced mutation (wild for the wild-type)". For example, the wild-type C domain of Protein A is represented by "C-wild", and a C domain variant containing the G29E mutation is represented by "C-G29E". Domain variants containing two mutations together are represented by indicating the two mutations together with a slash. For example, a C domain variant containing the G29E and S13L mutations is represented by "C-G29E/S13L". For proteins containing a plurality of monomeric domains connected together, a period (.) and the number of connected domains with "d" are further added. For example, a protein consisting of five connected C domain variants containing the G29A and S13L mutations is represented by "C-G29A/S13L.5d".

Example 1

Preparation of Expression Plasmids for Various Single-domain Type C Domain Variants Oligonucleotides respectively having the nucleotide sequences of SEQ ID Nos:6 and 7 were mixed and subjected to overlap PCR using a polymerase Blend Taq (TOYOBO CO., LTD.) in accordance with the attached protocol. A double-stranded DNA PCR product was extracted and purified by agarose electrophoresis, and cleaved using restriction enzymes BamHI and HindIII (both available from Takara Bio, Inc.). Another double-stranded DNA was obtained by PCR from oligonucleotides respectively having the nucleotide sequences of SEQ ID Nos:8 and 9 in the same manner as described above, and cleaved using restriction enzymes HindIII and EcoRI (both available from Takara Bio, Inc.).

These two double-stranded DNAs were subcloned into the BamHI/EcoRI site in a multiple cloning site of a plasmid vector pGEX-2T (GE health care, Japan). Specifically, the vector pGEX-2T was cleaved by the restriction enzymes BamHI and EcoRI, dephosphorylated by Alkaline Phosphatase (Takara Bio, Inc.), and mixed with the above two double-stranded DNAs which had been treated with the two restriction enzymes, and they were ligated with Ligation High (TOYOBO CO., LTD.) in accordance with the attached protocol. The DNAs of SEQ ID Nos:6, 7, 8, and 9 were designed such that the two double-stranded DNAs, when ligated through the HindIII cleavage sites and subcloned into pGEX-2T, encode the sequence of SEQ ID No:10 (C-K04R/K07E/G29A/K35H/K42R/K49Q/K50R/K58G.1d). E. coli HB101 cells (Takara Bio, Inc.) were transformed using pGEX-2T containing the DNA of SEQ ID No:10 (the ligation solution), and the plasmid DNA was amplified and extracted by a common method.

Quick change mutagenesis was performed using the expression plasmid obtained by the subcloning as a template, and two oligonucleotide primers selected from the primers of SEQ ID Nos:11 to 20 to produce expression plasmids containing an additional mutation. The quick change mutagenesis was performed in accordance with the protocol of Stratagene using Pfu Turbo DNA polymerase and the methylated DNA (template DNA) cleavage enzyme DpnI (all available from Stratagene).

Table 1 shows the oligonucleotide primer sequences of SEQ ID No:11 to 20, pairs of the primers used in the quick change mutagenesis, and introduced amino acid mutations. All the oligonucleotide primers were custom-synthesized products (Sigma-Aldrich Japan) unless otherwise specified.

The DNA base sequences of the expression plasmids were determined using a DNA sequencer 3130×1 Genetic Analyzer (Applied Biosystems). Using BigDye Terminator v. 1.1 Cycle Sequencing Kit (Applied Biosystems) in accordance with the attached protocol, PCR for sequencing of these plasmid DNAs was carried out, and the sequencing products were purified and sequenced. For the expression plasmids containing pGEX-2T as a vector, commercially-available pGEX 3' Sequencing Primer (GE health care, Japan) was used as a primer. The confirmed DNA sequences encoding the proteins of SEQ ID Nos:21 to 25 are shown as SEQ ID Nos:26 to 30, respectively.

Example 2

Expression and Purification of Single-domain Type C Domain Variants

Transformants capable of expressing the respective single-domain type C domain variants obtained in Example 1 in the form of GST fusion proteins were cultured in LB media containing ampicillin at 37° C. overnight. The liquid cultures were inoculated in 2xYT media (containing ampicillin) and incubated at 37° C. for about 2 hour. To the media, IPTG (isopropyl-1-thio-β-D-galactoside) was added

TABLE 1

Primer pairs and introduced amino acid mutations

| Introduced mutation | Sequence | | | |
|---|---|---|---|---|
| K7D | SEQ ID No: 11 | 5' | CAACCGTTTCAACGACGAACAACAAAATG | 3' |
|  | SEQ ID No: 12 | 5' | CATTTTGTTGTTCGTCGTTGAAACGGTTG | 3' |
| K7R | SEQ ID No: 13 | 5' | CAACCGTTTCAACCGGGAACAACAAAATG | 3' |
|  | SEQ ID No: 14 | 5' | CATTTTGTTGTTCCCGGTTGAAACGGTTG | 3' |
| K35R | SEQ ID No: 15 | 5' | CATCCAAAGCTTGCGCGACGATCCTTCAG | 3' |
|  | SEQ ID No: 16 | 5' | CTGAAGGATCGTCGCGCAAGCTTTGGATG | 3' |
| K49R/(K50R) | SEQ ID No: 17 | 5' | GCAGAAGCTCGGCGCCTAAAC | 3' |
|  | SEQ ID No: 18 | 5' | GTTTAGGCGCCGAGCTTCTGC | 3' |
| K49R/K50H | SEQ ID No: 19 | 5' | GCAGAAGCTCGGCACCTAAACGATG | 3' |
|  | SEQ ID No: 20 | 5' | CATCGTTTAGGTGCCGAGCTTCTGC | 3' |

An expression plasmid obtained by a quick change mutagenesis process can be used as a template for another quick change mutagenesis process. Accordingly, quick change mutagenesis was performed 1 to 3 times using different combinations of template plasmids and primers (5 combinations) to provide the respective expression plasmids. These expression plasmids were transformed into HB101 cells. In this manner, transformants for expression of variants were obtained. Based on preliminary analysis for expression, purification, and the like, expression plasmids and transformants encoding the following variants were selected and used in the examples described below.
C-K04R/K07R/G29A/K35R/K42R/K49R/K50R/K58G.1d (SEQ ID No:21)
C-K04R/K07R/G29A/K35R/K42R/K49Q/K50R/K58G.1d (SEQ ID No:22)
C-K04R/K07E/G29A/K35R/K42R/K49R/K50H/K58G.1d (SEQ ID No:23)
C-K04R/K07D/G29A/K35R/K42R/K49R/K50H/K58G.1d (SEQ ID No:24)
C-K04R/K07E/G29A/K35R/K42R/K49R/K50R/K58G.1d (SEQ ID No:25)

at a final concentration of 0.1 mM, followed by further incubation at 37° C. for 18 hours.

After the incubation, cells were collected by centrifugation and resuspended in 5 mL of PBS buffer. The cells were sonicated and centrifuged to separate a supernatant fraction (cell-free extract) and an insoluble fraction. The genes of interest were each incorporated into the multiple cloning site of pGEX-2T vector to express fusion proteins with GST at the N terminal. The fractions were analyzed by SDS electrophoresis. All the cell-free extracts prepared from the transformant cultures showed a protein band of about 33,000 molecular weight, which was presumed to be induced by IPTG.

The GST fusion proteins were purified (partially purified) from the cell-free extracts containing the GST fusion proteins by affinity chromatography using a GSTrap FF column (GE Healthcare, Japan), which has an affinity for GST. Each cell-free extract was charged into the GSTrap FF column, and the column was washed with a standard buffer (20 mM NaH$_2$PO$_4$—Na$_2$HPO$_4$, 150 mM NaCl, pH 7.4). Then, the target GST fusion proteins were eluted with an elution buffer (50 mM Tris-HCl, 20 mM glutathione, pH 8.0).

The genes were each incorporated into the multiple cloning site of pGEX-2T vector to encode, between GST and the target protein, an amino acid sequence that allows GST to be removed with Thrombin (available from GE Healthcare, Japan). GST was removed using Thrombin in accordance with the attached protocol. Finally, the target proteins were purified by gel filtration chromatography using a Superdex 75 10/300 GL column (GE health care, Japan). The reaction solutions were each charged into a Superdex 75 10/300 GL column equilibrated with the standard buffer to separate and purify the target proteins from separated GST and Thrombin. All the above protein purification processes by chromatography using the column were performed by an AKTAprime plus system (GE health care, Japan).

The purified protein solutions were analyzed by tricine-SDS electrophoresis, and each showed a band of about 7,000 molecular weight, which was presumed to be a band of the target protein. Based on the results of tricine-SDS electrophoresis, their purities were presumed to be as high as 90% or higher. The primary sequences of the proteins obtained in this example were sequences modified from the single-domain type C domain variants of SEQ ID No:21 to 25 in which Gly-Ser derived from the vector pGEX-2T and Ser were added to the N terminal and the C terminal, respectively.

Example 3

Analysis for Affinity of Single-domain Type C Domain Variants for Human IgG

The single-domain type C domain variants obtained in Example 2 were analyzed for affinity for an immunoglobulin with a biosensor Biacore 3000 (GE health care, Japan) utilizing surface plasmon resonance. In the present example, a human immunoglobulin G drug (hereinafter, referred to as human IgG) separated from human plasma was immobilized on a sensor chip, and each protein was added on the chip to detect an interaction between them.

The immobilization of the human IgG on the sensor chip CM5 was carried out by amine coupling using N-hydroxysuccinimide (NHS) and N-ethyl-N'-(3-dimethylaminopropyl)carbodiimide hydrochloride (EDC), and ethanolamine was used for blocking (both the sensor chip and the immobilization reagents are available from GE health care, Japan). The human IgG solution was prepared by dissolving Gammagard (Baxter) in a standard buffer (20 mM $NaH_2PO_4$—$Na_2HPO_4$, 150 mM NaCl, pH 7.4) to a concentration of 1.0 mg/mL. The human IgG solution was diluted to 1/100 in an immobilization buffer (10 mM $CH_3COOH$—$CH_3COONa$, pH 4.5), and the human IgG was immobilized on the sensor chip in accordance with the protocol attached to the Biacore 3000. A reference cell to be used as a negative control was also prepared by immobilizing ethanolamine on another flow cell on the chip after activation by EDC/NHS.

The single-domain type C domain variants were appropriately prepared at concentrations of 10 to 1000 nM using a running buffer (20 mM $NaH_2PO_4$—$Na_2HPO_4$, 150 mM NaCl, 0.005% P-20, pH 7.4) (solutions of three different protein concentrations were prepared for each variant), and each protein solution was added on the sensor chip at a flow rate of 20 μL/min for 30 seconds. A sensorgram of the binding reaction at 25° C. was sequentially plotted during the addition (binding phase, 90 seconds) and after the addition (dissociation phase, 90 seconds). After each analysis, the sensor chip was regenerated by adding 40 mM NaOH (for 15 seconds). This process was performed to remove the added proteins remaining on the sensor chip, and confirmed to substantially restore the binding activity of the immobilized human IgG to the original level. The affinity constant for human IgG ($K_A = k_{on}/k_{off}$) was calculated by performing a fitting analysis on each of the obtained binding reaction sensorgrams (the binding reaction sensorgrams obtained by subtracting the binding reaction sensorgram of the reference cell) using the 1:1 binding model in a software BIA evaluation attached to the system. The results are shown in Table 2.

TABLE 2

| Binding parameters of proteins to human IgG | |
|---|---|
| Single-domain type C domain variants | $K_A$ ($\times 10^7 M^{-1}$) |
| C-G29A.1d | 4.7 |
| C-K04R/K07R/G29A/K35R/K42R/K49R/K50R/K58G.1d | 4.8 |
| C-K04R/K07R/G29A/K35R/K42R/K49Q/K50R/K58G.1d | 3.3 |
| C-K04R/K07E/G29A/K35R/K42R/K49R/K50H/K58G.1d | 2.7 |
| C-K04R/K07D/G29A/K35R/K42R/K49R/K50H/K58G.1d | 1.3 |
| C-K04R/K07E/G29A/K35R/K42R/K49R/K50R/K58G.1d | 1.1 |

As shown in Table 2, the binding parameters of the single-domain type C domain variants to the human IgG were at similar levels to that of C-G29A.1d (Comparative Example 1). Specifically, the affinity constants of all the proteins for the human IgG fell in the range of $1.0 \times 10^7 M^{-1}$ to $5.0 \times 10^7 M^{-1}$ (the order of seventh power of 10).

Example 4

Mass Production of Ligand for Immobilization Experiment

In order to prepare a carrier on which C-K04R/K07R/G29A/K35R/K42R/K49R/K50R/K58G.1d (SEQ ID No:21) is immobilized as an IgG affinity ligand, the protein was expressed and purified using a *Brevibacillus* expression system that was able to express a large amount of this protein.

First, PCR was performed using a pGEX-2T expression plasmid encoding C-K04R/K07R/G29A/K35R/K42R/K49R/K50R/K58G.1d as a template, and oligonucleotide primers of SEQ ID Nos:31 and 32. The PCR product was purified and treated with restriction enzymes PstI (Takara Bio, Inc.) and EcoRI to prepare a double-stranded insert DNA.

The vector used as a template was pNK3260' that is a variant of a known *Brevibacillus* expression vector pNK3260 (WO 2006/004067), and designed such that a DNA encoding a target protein can be inserted into the PstI/EcoRI site. The vector pNK3260' was cleaved by the restriction enzymes PstI and EcoRI, and dephosphorylated by Alkaline Phosphatase, and mixed with the above double-stranded insert DNA, and they were ligated with Ligation High. In this manner, a *Brevibacillus* expression plasmid for C-K04R/K07R/G29A/K35R/K42R/K49R/K50R/K58G.1d was constructed. This plasmid vector was transformed into *Brevibacillus choshinensis* FY-1. The transformation was accomplished by a known electroporation method ("Biosci. Biotech. Biochem.", 1997, No. 61, 202-203). The *Brevibacillus choshinensis* FY-1 is a Phe- and Tyr-requiring strain obtained by mutating *Brevibacillus choshinensis* HPD31-OK (JP H06-296485 A).

The *Brevibacillus choshinensis* FY-1 recombinant cells were cultured with shaking for 3 days at 30° C. in 5 mL of 3YC medium (3% polypeptone, 0.2% yeast extract, 3% glucose, 0.01% magnesium sulfate, 0.001% iron sulfate, 0.001% manganese chloride, 0.0001% zinc chloride) containing 60 µg/mL neomycin.

The culture was centrifuged to remove cells, and the obtained culture supernatant was subjected to cation exchange chromatography using an SP Fast Flow column (GE Healthcare, Japan) to purify (partially purify) the target protein. Specifically, sodium acetate was added to the culture supernatant to a final concentration of 50 mM, and hydrochloric acid was also added to the culture supernatant to adjust the pH to 4.0. Then, the culture supernatant was charged to the SP Fast Flow column equilibrated with a cation exchange buffer A (50 mM $CH_3COOH$—$CH_3COONa$, pH 4.0). After washing the column with the cation exchange buffer A, the target protein was eluted and separated in the process of salt gradient elution using the cation exchange buffer A and a cation exchange buffer B (50 mM $CH_3COOH$—$CH_3COONa$, 1 M NaCl, pH 4.0). Next, the target protein was purified by anion exchange chromatography using a DEAE Fast Flow column (GE Healthcare, Japan). Specifically, the separated target protein solution was dialyzed with ultrapure water, and charged to the DEAE Fast Flow column equilibrated with an anion exchange buffer A (50 mM Tris-HCl, pH 8.0). After washing with the anion exchange buffer A, the target protein was eluted and separated in the process of salt gradient elution using the anion exchange buffer A and an anion exchange buffer B (50 mM Tris-HCl, 0.3 M NaCl, pH 8.0). The separated target protein solution was re-dialyzed with ultrapure water. In this manner, an aqueous solution containing only the target protein was obtained as a final purified sample. All the above protein purification processes by chromatography using the column were performed by an AKTAprime plus system.

The primary sequence of the ligand protein obtained by the use of this expression system was a sequence modified from C-K04R/K07R/G29A/K35R/K42R/K49R/K50R/K58G.1d of SEQ ID No:21 in which Ser-Lys was added at the C terminal. Namely, the ligand contained only one lysine residue at the C terminal.

Example 5

Preparation of Prototype Affinity Separation Matrix with Carrier on which Ligand is Immobilized An affinity separation matrix was formed by immobilizing the ligand prepared in Example 4 to a commercially-available coupling column for ligand immobilization which is designed for coupling through an amino group.

As a water-insoluble base material, a commercially-available 1-mL prepacked column "Hitrap NHS activated HP" (GE health care, Japan) was used. This column was already packed with a crosslinked agarose-based material having an active group that can be used for immobilization of a protein ligand through an amino group as a coupling functional group. The ligand was immobilized in accordance with the product manual of the column. The ligand was diluted to a final concentration of about 10 mg/mL in a coupling buffer (0.2 M $NaHCO_3$, 0.5 M NaCl, pH 8.3) to prepare a ligand diluted solution (1 mL). The procedure of running 2 mL of 1 mM HCl cooled in an ice bath at a flow rate of 1 mL/min was carried out three times to remove isopropanol in the column. Then, 1 mL of the sample diluted solution prepared above was immediately added at the same flow rate. The top and bottom of the column were sealed, and the column was then left at rest at 25° C. for 30 minutes. In this manner, the obtained protein was immobilized to the column. Thereafter, the column was opened, and 3 mL of the coupling buffer was run through the column at the same flow rate to recover unreacted ligand. Next, the procedure of running 2 mL of a blocking buffer (0.5 M ethanolamine, 0.5 M NaCl, pH 8.3) was carried out three times, and the procedure of running 2 mL of a washing buffer (0.1 M Acetate, 0.5 M NaCl, pH 4.0) was also carried out three times. Finally, 2 mL of a standard buffer (20 mM $NaH_2PO_4$—$Na_2HPO_4$, 150 mM NaCl, pH 7.4) was run through the column. Thus, the preparation of an affinity separation column was completed.

NHS replaced in the immobilization reaction is known to absorb at 280 nm. NHS was removed using a desalting column HiTrap Desalting 5 mL (GE health care, Japan), and the absorbance of pure unreacted ligand at 280 nm ($Abs_{280}$) was measured to calculate the immobilization yield. The use of HiTrap Desalting enabled components having a molecular weight of not less than 5,000 (namely, the ligand in this experiment) and components having a molecular weight of not more than 1,000 (replaced NHS) to be separated. Specifically, 500 µL of unreacted ligand was run through the HiTrap Desalting 5 mL, and 1 mL of the coupling buffer was also run therethrough. Then, 1.5 mL of the coupling buffer was further added, and 1.5 mL of the eluate flowing out was recovered and measured for absorbance at 280 nm. The concentration was calculated by the calculation formula (when the $Abs_{280}$ is 0.343, the concentration is 1 mg/mL) preliminary obtained by studies by HPLC or the biuret test. The ligand immobilized amount was found to be 6.6 mg/mL-gel, and the immobilization yield was found to be 67%.

Example 6

Evaluation of IgG Binding Capacity of Prototype Affinity Separation Matrix

In order to evaluate the human IgG binding capacity of the prototype affinity separation matrix, the prototype affinity separation matrix was measured for antibody dBC by an affinity chromatography experiment. Gamma globulin (Nichiyaku) was diluted with a standard buffer (20 mM Na-Pi, 150 mM NaCl, pH 7.4) to 1/150, and the resulting 1 mg/mL solution was used as a human IgG. The cell of the chromatography system AKTAprime plus was used to measure $Abs_{280}$ (100% $Abs_{280}$) while this solution was being run therethrough 100%. In the above procedure, 1 mL was regarded as 1 CV based on the size of HiTrap NHS Activated HP (1 mL) (φ 0.7×2.5 cm (0.96 mL)).

The prototype affinity separation matrix was connected to the chromatography system AKTAprime plus, and 5 CV of a standard buffer was run at 2.0 mL/min to equilibrate the column. Then, the human IgG solution was run at 1.9 mL/min (296 cm/h) until the monitored absorbance exceeded 5% of the 100% $Abs_{280}$. Thereafter, 13 CV of the standard buffer was run at 2.0 mL/min, and then 15 CV of an elution buffer (35 mM Acetate, pH 3.5) was run to elute human IgG. The total amount of the human IgG flowed until the monitored absorbance exceeded 5% of the 100% $Abs_{280}$ was regarded as antibody dBC (antibody 5% dBC).

The evaluation results of the prototype affinity separation matrix were shown in Table 3.

TABLE 3

| Prototype ID | Number of Lys in ligand [number of residues] | Antibody affinity constant $K_A$ [×10$^7$M$^{-1}$] | Ligand immobilized amount [mg/mL-gel] | 5% antibody dBC [mg/mL-gel] |
|---|---|---|---|---|
| Comparison 1 | 7 | 2.2 | 6.6 | 17.5 |
| Prototype 1 | 1 (C terminal) | 2.2 | 6.5 | 25.7 |

Immobilized ligand
Comparison 1: C-G29A/S33E.1d
Prototype 1: C-K04R/K07R/G29A/K35R/K42R/K49R/K50R/K58G.1d The antibody 5% dBC of the prototype affinity separation matrix was found to be 25.7 mg/mL-gel. In spite of substantially the same ligand immobilized amount, the antibody 5% dBC of the prototype affinity separation matrix of Comparative Example 1 was found to be 17.5 mg/mL-gel. Based on the results of the experiment, the ligand of the present invention was presumed to significantly improve the antibody binding capacity per unit ligand immobilized amount. The affinity constant of the ligand of the prototype 1 for the antibody was slightly different from that of Example 3 (Table 2). This difference can be explained by the slight difference of the measured samples (due to the change of the expression system and addition of Lys to the C terminal in Example 4), and is within a tolerance range. The affinity constants for the antibody in the table were measured in the manner as described in Example 3.

Example 7

Preparation of Multi-domain Connected C Domain Variants

The technique of the present invention can be used for multiple domains connected in tandem. Also, the technique can be used for tandem connected proteins further engineered by a change in the sequence of a linker between domains, a change in the terminal sequence to be involved in immobilization, and/or other mutations. The following processes (1) to (4) describe how expression plasmids for multi-domain connected C domain variants were prepared in this example.

(1) C-K04R/K07R/G29A/K35R/K42R/K49R/K50R/K58G.4d (or 2d)_type.1

The same procedure as in Example 4 was performed using an expression plasmid prepared through STEPs. 1 to 2 described below to provide a ligand protein having a primary sequence of SEQ ID No:33. Specifically, Ser was added downstream of each domain (the domains were connected through Ser functioning as a linker), and Lys was added to the C terminal of the protein. The DNA sequence of this expression plasmid is shown as SEQ ID No:34.

[STEP. 1] Single-domain Type→Two-domain Type

Process 1) PCR was performed using the expression plasmid encoding C-K04R/K07R/G29A/K35R/K42R/K49R/K50R/K58G.1d (SEQ ID No:21) obtained in Example 1 as a template, and oligonucleotide primers of SEQ ID Nos:31 and 35. The PCR product was purified and treated with the restriction enzymes PstI and BamHI. In this manner, a double-stranded insert DNA was prepared.

Process 2) A double-stranded insert DNA was prepared by PCR using the same template and oligonucleotide primers of SEQ ID Nos:32 and 36, purifying the PCR product, and treating it with restriction enzymes BglII (Takara Bio, Inc.) and EcoRI.

Process 3) These two double-stranded insert DNAs were mixed with pNK3260' of Example 4 which had been treated with the restriction enzymes (PstI and EcoRI) and dephosphorylated, and they were ligated with Ligation High. In this manner, an expression plasmid for two tandem connected domains C-K04R/K07R/G29A/K35R/K42R/K49R/K50R/K58G.2d_type.1 was constructed.

[STEP. 2] Two-domain Type→Four-domain Type

Process 1) PCR was performed using the expression plasmid for C-K04R/K07R/G29A/K35R/K42R/K49R/K50R/K58G.2d_type.1 as a template, and oligonucleotide primers of SEQ ID Nos:35 and 37, and the PCR product was purified and treated with restriction enzymes BglII and EcoRI. In this manner, a double-stranded insert DNA was prepared.

Process 2) The expression plasmid for C-K04R/K07R/G29A/K35R/K42R/K49R/K50R/K58G.2d (this plasmid was the same as the template used in the PCR) was treated with restriction enzymes (BamHI/EcoRI), and dephosphorylated.

Process 3) The purified products obtained in Processes 1 and 2 were mixed and ligated. As a result, an expression plasmid for four tandem connected C domain variants C-K04R/K07R/G29A/K35R/K42R/K49R/K50R/K58G.4d was constructed.

(2) C-K04R/K07R/G29A/K35R/K42R/K49R/K50R/K58G.4d (or 2d)_type.2

The same procedure as in Example 4 was performed using an expression plasmid prepared through STEPs. 1 to 2 described below to provide a ligand protein having a primary sequence of SEQ ID No:38. Specifically, the domains were connected directly without a linker, and Lys was substituted for Gly at the C terminal. In other words, the Lys residue was conserved without mutation only in the most C-terminal domain (fourth domain). This engineering is also included in the scope of the present invention. This engineering was conveniently selected to obtain a ligand containing the same number of amino acid residues as that of the comparative multi-domain connected C domain variant in which the Lys residues are conserved without mutation, namely, to avoid unnecessary differences from the comparative variant as much as possible. The DNA sequence of this expression plasmid is shown as SEQ ID No:39.

[STEP. 1] Single-domain Type→Two-domain Type

Process 1) PCR was performed using the same expression plasmid as that used in the case (1) as a template, and oligonucleotide primers of SEQ ID Nos:31 and 40, and the PCR product was purified and treated with restriction enzymes PstI and cfr13I (Takara Bio, Inc.). In this manner, a double-stranded insert DNA was prepared.

Process 2) A double-stranded insert DNA was prepared by PCR using the same template and oligonucleotide primers of SEQ ID Nos:41 and 42, purifying the PCR product, and treating it with restriction enzymes cfr13I and EcoRI.

Process 3) These two double-stranded insert DNAs were mixed with pNK3260' of Example 4 which had been treated with the restriction enzymes (PstI and EcoRI) and dephosphorylated, and they were ligated. In this manner, an expression plasmid for C-K04R/K07R/G29A/K35R/K42R/K49R/K50R/K58G.2d_type.2 was constructed.

[STEP. 2] Two-domain Type→Four-domain Type

Process 1) Quick change mutagenesis was performed using the expression plasmid for C-K04R/K07R/G29A/K35R/K42R/K49R/K50R/K58G.2d_type.2 as a template and oligonucleotide primers of SEQ ID Nos:43 and 44 to provide a modified expression plasmid without the cfr13I site.

Process 2) A double-stranded insert DNA was prepared by PCR using the same template and oligonucleotide primers of SEQ ID Nos:40 and 45, purifying the PCR product, and treating it with restriction enzymes PstI and cfr13I.

Process 3) A double-stranded insert DNA was prepared by PCR using the same template as that used in the Process 2 and oligonucleotide primers of SEQ ID Nos:41 and 42, purifying the PCR product, and treating it with restriction enzymes cfr13I and EcoRI.

Process 4) The purified products obtained in Processes 2 and 3 were mixed and ligated. In this manner, an expression plasmid for C-K04R/K07R/G29A/K35R/K42R/K49R/K50R/K58G.4d_type.2 was constructed.

(3) C-K04R/K07R/G29A/K35R/K42R/K49R/K50R/K58R.4d (or 2d)_type.2

The same procedure as in Example 4 was performed using an expression plasmid prepared through STEPs. 1 to 2 described below to provide a ligand protein having a primary sequence of SEQ ID No:46. Specifically, the sequence was the same as that of the case (2), except that K58R was introduced instead of K58G in all the domains except the most C-terminal domain (fourth domain). Namely, all the lysine residues in the C domain variant were replaced with arginine. Since Lys for immobilization was added, the lysine residue at the C terminal out of all the 28 lysine residues was not replaced with arginine and conserved in the resulting sequence. The DNA sequence of this expression plasmid is shown as SEQ ID No:47.

[STEP. 1] Single-domain Type→Two-domain Type

This step is the same as [STEP. 1] of the case (2). Oligonucleotide primers of SEQ ID Nos:31 and 48 were used in Process 1), and oligonucleotide primers of SEQ ID Nos:42 and 49 were used in Process 2). Restriction enzymes PstI and XhoI (Takara Bio, Inc.) were used in Process 1), and XhoI and EcoRI were used in Process 2). Finally, an expression plasmid for C-K04R/K07R/G29A/K35R/K42R/K49R/K50R/K58R.2d_type.2 was constructed.

[STEP. 2] Two-domain Type→Four-domain Type

This step is the same as [STEP. 2] of the case (2). The expression plasmid constructed in [STEP. 1] of the case (3) was used as a template in Process 1). Oligonucleotide primers of SEQ ID Nos:50 and 51 were used in Process 1), oligonucleotide primers of SEQ ID Nos:45 and 48 were used in Process 2), and oligonucleotide primers of SEQ ID Nos:42 and 49 were used in Process 3). Restriction enzymes PstI and XhoI were used in Process 2), and XhoI and EcoRI were used in Process 3). Finally, an expression plasmid for C-K04R/K07R/G29A/K35R/K42R/K49R/K50R/K58R.2d_type.2 was constructed.

(4) C-K04R/K07R/G29A/S33E/K35R/K42R/K49R/K50R/K58R.4d (or 2d)_type.2

The same procedure as in Example 4 was performed using an expression plasmid prepared through STEPs. 0 to 2 described below to provide a ligand protein having a primary sequence of SEQ ID No:52. Specifically, the mutation S33E was introduced to all the domains of the construct of (3). The DNA sequence of this expression plasmid is shown as SEQ ID No:53.

[STEP. 0] Introduction of Mutation to Single-domain Type

Quick change mutagenesis was performed using the expression plasmid obtained in Example 1 and pGEX-2T containing a DNA encoding the sequence of SEQ ID No:21 as a template, and oligonucleotide primers of SEQ ID Nos:54 and 55 to construct a mutated expression plasmid.

[STEP. 1] Single-domain Type→Double-domain Type

This step is the same as STEP. 1 of the case (3). Finally, an expression plasmid for C-K04R/K07R/G29A/S33E/K35R/K42R/K49R/K50R/K58R.2d_type.2 was constructed.

[STEP. 2] Two-domain Type→Four-domain Type

This step is the same as STEP. 2 of the case (3). Finally, an expression plasmid for C-K04R/K07R/G29A/S33E/K35R/K42R/K49R/K50R/K58R.4d_type.2 was constructed.

These expression plasmids were transformed into *Brevibacillus choshinensis* FY-1 in the same manner as in Example 4. The transformants were used to produce large amounts of the multi-domain connected C domain variants in the same manner as in Example 4.

Example 8

Evaluation of Stability of Novel Polypeptide Against Alkali by SDS-PAGE Analysis The stability against alkali was evaluated by incubating the polypeptides obtained in Example 7 under an alkali condition for a predetermined time period, and comparing their bands after this treatment on SDS-PAGE.

The alkali treatment was performed as follows. NaOH was added to the polypeptides (each 200 μM) to a final peptide concentration of 0.5 M, and the solutions were incubated at 25° C. for 4, 8, and 24 hours. To the polypeptide solutions, 0.5 M HCl (in a predetermined amount that was confirmed to adjust the pH to neutral) was added to neutralize the solutions. Thus, SDS-PAGE samples were prepared. The SDS-PAGE samples before the alkali treatment (0 hour after treatment) were controlled to have the same polypeptide concentration and solution composition by adding a mixture of the NaOH solution for the alkali treatment and the HCl solution for the neutralization treatment. SDS-PAGE was performed using a power-mounted mini-slab size electrophoresis bath "pageRun" and a 15% polyacrylamide precast gel "e•PAGEL" (both available from ATTO CORPORATION) in accordance with the attached manual (common method). The electrophoresis gels were dyed and destained, electronically imaged with an imaging system ChemiDoc XRS (Bio-Rad Laboratories, Inc.), and then analyzed with a software Quantity One (Bio-Rad Laboratories, Inc.) attached to a band analyzer (densitometry) in accordance with a manual. FIG. 2 is an electronic image obtained by the SDS-PAGE.

The results of the band intensity ratio of 24 hours after the alkali treatment (the remaining intensity as calculated based on the intensity before the alkali treatment regarded as 100%) were as follows: the ratio of the known highly alkali-resistant polypeptide (Comparative Example 1, C-G29A.2d) was 55.0%; the ratio of the polypeptide C-K04R/K07R/G29A/K35R/K42R/K49R/K50R/K58G.2d_type.2 was 60.9%; and the ratio of the polypeptide C-K04R/K07R/G29A/K35R/K42R/K49R/K50R/K58R.2d_type.2 was 91.6%.

Thus, the polypeptides of the present invention were found to be highly stable under a severe alkali condition. In particular, the polypeptide C-K04R/K07R/G29A/K35R/K42R/K49R/K50R/K58R.2d_type.2 showed only a slight change in the band intensity (99.8% of the intensity was maintained) even after the 4-hour incubation in 0.5 M NaOH at 25° C., and therefore was concluded to be a very useful polypeptide in many applications.

Example 9

Characterization of Multi-domain Connected C Domain Variants by Gel Filtration Chromatography The C-K04R/K07R/G29A/K35R/K42R/K49R/K50R/K58G.4d (or .2d) type.1 peptides obtained in Example 7 were analyzed by gel filtration chromatography for apparent molecular weight based on the retention time (the position of an elution peak).

A gel filtration column "Superdex 75 10/300 GL" (GE health care, Japan) was attached to a chromatography system AKTAprime plus, and equilibrated with a standard buffer. A sample was charged to the column, and then the standard buffer was run again to determine the retention time (the position of the elution peak). These operations were continuously performed, and all the solutions were run at a constant flow rate of 0.5 mL/min. In order to generate a standard curve for calculation of the apparent molecular weight based on the retention time, the retention times of three molecular weight marker proteins (see Table 4) were determined by the same procedure. The results of the molecular weight markers were plotted on a graph where the vertical axis y represents log (MW), and the horizontal axis x represents the retention time (min), and a standard curve $y=-0.0834x+6.5794$ was generated (MW represents the molecular weight [Da]). The apparent molecular weight was determined based on this standard curve.

Table 4 is provided for a comparison of the retention time and apparent molecular weight between C-K04R/K07R/G29A/K35R/K42R/K49R/K50R/K58G.2d_type.1 and the two-domain type of C-G29A/S33E and between C-K04R/K07R/G29A/K35R/K42R/K49R/K50R/K58G.4d_type.1 and the four-domain type of C-G29A/S33E.

TABLE 4

| C domain variant | Actual molecular weight (kDa) | Retention time (min) | Apparent molecular weight (kDa) |
|---|---|---|---|
| C-G29A/S33E.2d_type.2 | 13.4 | 26.05 | 25.4 |
| C-K04R/K07R/G29A/K35R/K42R/K49R/K50R/K58G.2d_type.1 | 13.8 | 27.13 | 20.7 |
| C-G29A/S33E.4d_type.2 | 26.7 | 22.73 | 48.1 |
| C-K04R/K07R/G29A/K35R/K42R/K49R/K50R/K58G.4d_type.1 | 27.3 | 24.27 | 35.8 |
| (Reference) molecular weight marker | | | |
| Ribonuclease A | 13.7 | 29.31 | 13.6 |
| Ovalbumin | 43 | 23.16 | 44.3 |
| BSA (Bovine Serum Albumin) | 66 | 21.21 | 64.5 |

The retention times of the proteins of the present invention were likely to be longer than those of the C domain variants without substitutions for Lys. Generally, a protein whose actual molecular weight and apparent molecular weight estimated from its retention time are closer is thought to be a protein of a more globular standard shape, and a protein whose apparent molecular weight is larger than its actual molecular weight is thought to be a protein of a shape different from the standard globular shape (e.g. a protein of a three-dimensionally wide shape). Protein A (multi-domain type C domain) is thought to have a shape different from the shape of standard globular proteins, and the variants obtained by the present invention are also thought to have this feature. However, their apparent molecular weights were certainly reduced by the introduced mutations. This suggests that the introduced mutations might make their whole three-dimensional structure slightly compact. Accordingly, it is suggested that the proteins of the present invention may be more complicatedly folded into a compact three-dimensional structure.

Example 10

Preparation and Evaluation of Prototype Carrier on which Multi-domain Connected C Domain Variant is Immobilized Prototype carriers on which the variants obtained in Example 7 were respectively immobilized were prepared in the same manner as in Example 5, and the same procedure as in Example 6 was performed to evaluate the binding ability of prototype affinity separation matrices to human IgG. Although both the expression plasmids for the two-domain connected (2d) type and the four-domain connected (4d) type were prepared in Example 6, only the following ligands were prepared by the *Brevibacillus* expression system: the four-domain connected type for (1); and the two-domain connected (2d) type for (2) to (4). Not all the ligand solutions used for the preparation of the prototype affinity separation matrices had a concentration of 10 mg/mL. The detail is omitted, and only the ligand immobilized amounts, which are an important factor, were shown in the table.

Table 5 shows the results of evaluation of the binding ability to human IgG of the prototype affinity separation matrix of (1) C-K04R/K07R/G29A/K35R/K42R/K49R/K50R/K58G.4d_type.1 of Example 7.

TABLE 5

| Prototype ID | Number of Lys in ligand [number of residues] | Antibody affinity constant $K_A$ [$\times 10^8 M^{-1}$] | Ligand immobilized amount [mg/mL-gel] | 5% antibody dBC [mg/mL-gel] |
|---|---|---|---|---|
| Comparison 2 | 28 | 17 | 4.8 | 25.4 |
| Prototype 2 | 1 (C terminal) | 7.5 | 3.7 | 27.1 |

Immobilized ligand
Comparison 2: C-G29A.4d_type.1
Prototype 2: C-K04R/K07R/G29A/K35R/K42R/K49R/K50R/K58G.4d_type.1

The prototype affinity separation matrix to which the multi-domain connected C domain variant of the present invention was immobilized showed a significantly high antibody dBC than the comparative matrix in spite of its significantly low ligand immobilized amount.

Table 6 shows the results of the binding ability to human IgG of the prototype affinity separation matrices to which (2) C-K04R/K07R/G29A/K35R/K42R/K49R/K50R/K58G.2d_type.2 and (3) C-K04R/K07R/G29A/K35R/K42R/K49R/K50R/K58R.2d_type.2 of Example 7 were respectively immobilized. The affinity constants for the antibody shown in the table were obtained in accordance with Example 3.

TABLE 6

| Prototype ID | Number of Lys in ligand [number of residues] | Antibody affinity constant $K_A$ [$\times 10^8 M^{-1}$] | Ligand immobilized amount [mg/mL-gel] | 5% antibody dBC [mg/mL-gel] |
|---|---|---|---|---|
| Comparison 3 | 14 | 2.4 | 6.9 | 22.3 |
| Prototype 3 | 1 (C terminal) | 2.1 | 6.0 | 26.5 |
| Prototype 4 | 1 (C terminal) | 2.6 | 6.0 | 27.4 |

Immobilized ligand
Comparison 3: C-G29A/S33E.2d_type.2
Prototype 3: C-K04R/K07R/G29A/K35R/K42R/K49R/K50R/K58G.2d_type.2
Prototype 4: C-K04R/K07R/G29A/K35R/K42R/K49R/K50R/K58R.2d_type.2

The ligand immobilized amounts of the prototype affinity separation matrices were substantially the same as that of the comparison 3, but the prototype affinity separation matrices nevertheless showed a significantly high antibody dBC. The experimental results revealed that the multi-domain connected ligands of the present invention produced the same effect of significantly improving the antibody binding capacity per unit ligand immobilized amount, regardless of a slight difference in connection (linker residues between domains) and a slight difference in the lysine replacement mutations. The experimental results also revealed that regardless of the number of connected domains, the effect of improving the antibody dBC was produced. Their degree of improvement in the antibody dBC was slightly smaller than that of the single-domain type. However, the values compared are measures of the capacity for accepting the antibody, and it is natural that the number of domains and the base material for immobilization affect the degree of improvement. The affinity constants for the antibody shown in the table were obtained in accordance with Example 3.

Example 11

Preparation of Two-domain Type C Domain Variants

Expression plasmids for variants different from variants of SEQ ID Nos:21 to 25 of Example 1 were prepared using the expression plasmid encoding SEQ ID No:10 (C-K04R/K07E/G29A/K35H/K42R/K49Q/K50R/K58G.1d) obtained in Example 1 as a template, the primers of Example 1 shown in Table 1, and the primers shown in Table 7. Mutations were introduced by quick change mutagenesis in the same manner as in Example 1. Table 7 shows the combination of the primer pair not shown in Table 1 and the introduced amino acid mutation.

TABLE 7

| Introduced mutation | Sequence |
|---|---|
| K35I | SEQ ID No: 56 5' CCTTCATCCAAATCTTGCGCGACG 3'<br>SEQ ID No: 57 5' CGTCGCGCAAGATTTGGATGAAGG 3' |

The following shows expressed variants.
C-K04R/K07R/G29A/K35I/K42R/K49Q/K50R/K58G.1d (SEQ ID No:58)
C-K04R/K07D/G29A/K35R/K42R/K49Q/K50R/K58G.1d (SEQ ID No:59)
C-K04R/K07R/G29A/K35I/K42R/K49R/K50R/K58G.1d (SEQ ID No:60)
C-K04R/K07R/G29A/K35H/K42R/K49Q/K50R/K58G.1d (SEQ ID No:61)
C-K04R/K07E/G29A/K35R/K42R/K49Q/K50R/K58G.1d (SEQ ID No:62)
C-K04R/K07R/G29A/K35H/K42R/K49R/K50R/K58G.1d (SEQ ID No:63)
C-K04R/K07D/G29A/K35R/K42R/K49R/K50R/K58G.1d (SEQ ID No:64)

Expression plasmids for the two-domain type (2d_type.2) were prepared in the manner described in [STEP. 1] of the case (3) in Example 7 using the expression plasmids for the above variants and the expression plasmids for SEQ ID Nos:22, 24, and 25 described in Example 1. The multi-domain connected C domain variants used in the following example were the plasmid obtained in Example 7 and the following plasmids.

C-K04R/K07R/G29A/K35R/K42R/K49R/K50R/K58R.2d_type2 (SEQ ID No:65)
C-K04R/K07R/G29A/K35R/K42R/K49Q/K50R/K58R.2d_type2 (SEQ ID No:66)
C-K04R/K07D/G29A/K35R/K42R/K49R/K50H/K58R.2d_type2 (SEQ ID No:67)
C-K04R/K07E/G29A/K35R/K42R/K49R/K50R/K58R.2d_type2 (SEQ ID No:68)
C-K04R/K07R/G29A/K35I/K42R/K49Q/K50R/K58R.2d_type2 (SEQ ID No:69)
C-K04R/K07D/G29A/K35R/K42R/K49Q/K50R/K58R.2d_type2 (SEQ ID No:70)
C-K04R/K07R/G29A/K35I/K42R/K49R/K50R/K58R.2d_type2 (SEQ ID No:71)
C-K04R/K07R/G29A/K35H/K42R/K49Q/K50R/K58R.2d_type2 (SEQ ID No:72)
C-K04R/K07E/G29A/K35R/K42R/K49Q/K50R/K58R.2d_type2 (SEQ ID No:73)
C-K04R/K07R/G29A/K35H/K42R/K49R/K50R/K58R.2d_type2 (SEQ ID No:74)
C-K04R/K07D/G29A/K35R/K42R/K49R/K50R/K58R.2d_type2 (SEQ ID No:75)

These expression plasmids were used to express the variants using recombinant *Brevibacillus choshinensis* FY-1 cells in the same manner as in Example 4, and the variants were purified in the same manner as in Example 4.

Example 12

Analysis for Affinity of Two-domain Type C Domain Variants for Human IgG

The two-domain type C domain variants were analyzed for affinity for human IgG with Biacore in accordance with the procedure described in Example 3. The two-domain type C domain variants were each diluted with a running buffer to solutions of 3 to 6 different concentrations within the range of 0.1 to 1000 nM, and these solutions were added to a sensor chip. Although the two-domain type and the single-domain type differ in the connecting mode (stoichiometric mixture ratio), the fitting analysis using the 1:1 binding model was performed in the same manner as in Example 3. Table 8 shows the calculated affinity constants for human IgG.

TABLE 8

Binding parameter of proteins to human IgG

| Two-domain type C domain varinat | $K_A$ (×10$^8$M$^{-1}$) |
|---|---|
| C-K04R/K07R/G29A/K35R/K42R/K49R/K50R/K58R.2d_type2 | 14 |
| C-K04R/K07R/G29A/K35R/K42R/K49Q/K50R/K58R.2d_type2 | 31 |
| C-K04R/K07D/G29A/K35R/K42R/K49R/K50H/K58R.2d_type2 | 19 |
| C-K04R/K07E/G29A/K35R/K42R/K49R/K50R/K58R.2d_type2 | 23 |
| C-K04R/K07R/G29A/K35I/K42R/K49Q/K50R/K58R.2d_type2 | 12 |
| C-K04R/K07D/G29A/K35R/K42R/K49Q/K50R/K58R.2d_type2 | 16 |
| C-K04R/K07R/G29A/K35I/K42R/K49R/K50R/K58R.2d_type2 | 9.7 |
| C-K04R/K07R/G29A/K35H/K42R/K49Q/K50R/K58R.2d_type2 | 6.8 |
| C-K04R/K07E/G29A/K35R/K42R/K49Q/K50R/K58R.2d_type2 | 32 |
| C-K04R/K07R/G29A/K35H/K42R/K49R/K50R/K58R.2d_type2 | 6.9 |
| C-K04R/K07D/G29A/K35R/K42R/K49R/K50R/K58R.2d_type2 | 14 |

All the proteins had an affinity constant for human IgG within the range of 5.0×10$^8$ M to 5.0×10$^9$ M. This suggests that a variety of combinations of replacement mutations of lysine residues with another amino acid are acceptable. The antibody affinity constant of the C-K04R/K07R/G29A/K35R/K42R/K49R/K50R/K58R.2d_type2 is different from that shown in Table 5 (7.5×10$^8$ M$^{-1}$). This may be because a new sensor chip was used in this experiment, and this difference of the antibody affinity constant is in the range of expectable error.

The two-domain type C domain variants obtained in Example 11 were also evaluated for alkali resistance by SDS-PAGE in the same manner as in Example 8. FIG. 3 shows an electronic image obtained by SDS-PAGE.

The results of the band intensity ratio of 24 hours after the alkali treatment were as follows.

C-K04R/K07R/G29A/K35R/K42R/K49Q/K50R/K58R.2d_type2: 73.4%
C-K04R/K07R/G29A/K35I/K42R/K49Q/K50R/K58R.2d_type2: 79.0%
C-K04R/K07R/G29A/K35I/K42R/K49R/K50R/K58R.2d_type2: 85.6%
C-K04R/K07R/G29A/K35H/K42R/K49R/K50R/K58R.2d_type2: 82.8%

Thus, these polypeptides were found to be highly stable under a severe alkali condition.

Example 13

Preparation and Evaluation of Multi-domain Connected C Domain Variant with Mutation at Ser-33/Asp-36

A plurality of constructs encoding a multi-domain connected C domain variant with a mutation at Ser-33 or Asp-36 were prepared in the same manner as described in the case (4) of Example 7. Table 9 shows the introduced mutations and the sequences of the oligonucleotide primers used in [STEP. 0] of the case (4) in Example 7. The template plasmids used in this step of the present example were expression plasmid constructs for SEQ ID Nos:21, 22, and 63.

TABLE 9

Primer pairs and introduced amino acid mutations

| Introduced mutation | Sequence | | |
|---|---|---|---|
| S33E/(K35R) | SEQ ID No: 76 | 5' | CTTCATCCAAGAGTTGCGCGAC 3' |
| | SEQ ID No: 77 | 5' | GTCGCGCAACTCTTGGATGAAG 3' |
| S33L/(K35R) | SEQ ID No: 78 | 5' | CTTCATCCAACTGTTGCGCGAC 3' |
| | SEQ ID No: 79 | 5' | GTCGCGCAACAGTTGGATGAAG 3' |
| (K35R)/D36I | SEQ ID No: 80 | 5' | GCTTGCGCATCGATCCTTCAG 3' |
| | SEQ ID No: 81 | 5' | CTGAAGGATCGATGCGCAAGC 3' |
| S33Q/(K35R) | SEQ ID No: 82 | 5' | CCTTCATCCAACAGTTGCGCGACG 3' |
| | SEQ ID No: 83 | 5' | CGTCGCGCAACTGTTGGATGAAGG 3' |
| S33H/(K35H) | SEQ ID No: 84 | 5' | CCTTCATCCAACATTTGCACGACG 3' |
| | SEQ ID No: 85 | 5' | CGTCGTGCAAATGTTGGATGAAGG 3' |
| S33R/(K35H) | SEQ ID No: 86 | 5' | CCTTCATCCAACGTTTGCACGACG 3' |
| | SEQ ID No: 87 | 5' | CGTCGTGCAAACGTTGGATGAAGG 3' |

The following two-domain type and four-domain type C domain variants including the variants prepared in the case (4) of Example 7 were actually prepared.

C-K04R/K07R/G29A/S33E/K35R/K42R/K49R/K50R/K58R.2d_type2 (SEQ ID No:88)
C-K04R/K07D/G29A/S33L/K35R/K42R/K49R/K50R/K58R.2d_type2 (SEQ ID No:89)
C-K04R/K07E/G29A/K35R/D36I/K42R/K49R/K50R/K58R.2d_type2 (SEQ ID No:90)
C-K04R/K07R/G29A/S33E/K35R/K42R/K49R/K50R/K58R.4d_type2 (SEQ ID No:52)
C-K04R/K07R/G29A/S33Q/K35R/K42R/K49Q/K50R/K58R.4d_type2 (SEQ ID No:91)
C-K04R/K07R/G29A/S33H/K35H/K42R/K49R/K50R/K58R.4d_type2 (SEQ ID No:92)
C-K04R/K07R/G29A/S33R/K35H/K42R/K49R/K50R/K58R.4d_type2 (SEQ ID No:93)

The variants were expressed using recombinant *Brevibacillus choshinensis* FY-1, and purified in the same manner as in Example 4.

The C domain variants were analyzed for affinity for human IgG with Biacore in accordance with the procedure described in Example 3. The C domain variants were each diluted with a running buffer to solutions of 3 to 6 different concentrations within the range of 0.1 to 1000 nM, and these solutions were added to a sensor chip. Although the two-domain type and the single-domain type differ in the connecting mode (stoichiometric mixture ratio), the fitting analysis using the 1:1 binding model was performed in the same manner as in Example 3. Table 10 shows the calculated affinity constants for human IgG.

TABLE 10

| Binding parameter of proteins to human IgG | |
|---|---|
| Two-domain type C domain variant | $K_A$ ($\times 10^8 M^{-1}$) |
| (Comparative Example 1) C-G29A/S33E.2d | 2.4 |
| C-K04R/K07R/G29A/S33E/K35R/K42R/K49R/K50R/K58R.2d_type2 | 4.3 |
| C-K04R/K07D/G29A/S33L/K35R/K42R/K49R/K50R/K58R.2d_type2 | 3.6 |
| C-K04R/K07E/G29A/K35R/D36I/K42R/K49R/K50R/K58R.2d_type2 | 3.6 |
| Four-domain type C domain variant | $k_{on}$ ($\times 10^6 M^{-1} s^{-1}$) |
| C-K04R/K07R/G29A/S33E/K35R/K42R/K49R/K50R/K58R.4d_type2 | 3.5 |
| C-K04R/K07R/G29A/S33Q/K35R/K42R/K49Q/K50R/K58R.4d_type2 | 1.5 |
| C-K04R/K07R/G29A/S33H/K35H/K42R/K49R/K50R/K58R.4d_type2 | 1.2 |
| C-K04R/K07R/G29A/S33R/K35H/K42R/K49R/K50R/K58R.4d_type2 | 1.5 |

All the two-domain type C domain variants had an affinity constant for human IgG within the range of $1.0 \times 10^8$ M to $1.0 \times 10^9$ M. Since the four-domain type C domain variants bind to the antibody more strongly than the two-domain type variants, and dissociate very slowly, the dissociation rate constant ($k_{off}$) of these variants could not be accurately calculated. Accordingly, the four-domain type C domain variants could not be appropriately compared in terms of the antibody affinity constant ($K_A = k_{on}/k_{off}$), and they were compared in terms of the association rate constant ($k_{on}$). The four-domain type C domain variants had a similar association rate constant. This suggests that the variants of the present invention produce the same effects even though they differ in the mutation amino acid introduced instead of Ser-33 in the sequence, amino acids substituted for Lys residues, and the combination of these.

Affinity separation matrices were prepared using these two-domain type C domain variants in the same manner as in Example 6, and evaluated for the binding ability to human IgG in the same manner as in Example 6. Table 11 shows the immobilized amounts of the two-domain type C domain variants and the results of evaluation of the binding ability of the prototype affinity separation matrices to human IgG.

TABLE 11

| Prototype ID | Number of Lys in ligand [number of residues] | Antibody affinity constant $K_A$ [$\times 10^8 M^{-1}$] | Ligand immobilized amount [mg/mL-gel] | 5% antibody dBC [mg/mL-gel] |
|---|---|---|---|---|
| Comparison 3 | 14 | 2.4 | 6.9 | 22.3 |
| Prototype 5 | 1 (C terminal) | 4.3 | 6.4 | 28.3 |
| Prototype 6 | 1 (C terminal) | 3.6 | 6.6 | 29.3 |
| Prototype 7 | 1 (C terminal) | 3.6 | 6.8 | 31.3 |

Immobilized ligand
Comparison 3: C-G29A/S33E.2d_type.2
Prototype 5: C-K04R/K07R/G29A/S33E/K35R/K42R/K49R/K50R/K58R.2d_type2
Prototype 6: C-K04R/K07D/G29A/S33L/K35R/K42R/K49R/K50H/K58R.2d_type2
Prototype 7: C-K04R/K07E/G29A/K35R/D36I/K42R/K49R/K50R/K58R.2d_type2

The prototype affinity separation matrices had a significantly high antibody dBC than the comparative matrix in spite of their similar ligand immobilized amounts. It was also revealed that proteins in which all the Lys residues in the immunoglobulin-binding domains of Protein A are replaced with other amino acids produce the effects of the present invention even when two or more amino acids other than the Lys residues are also replaced.

Example 14

Evaluation of Alkali Resistance of Prototype Affinity Separation Matrices

The affinity separation matrices to which the ligands were immobilized were evaluated for alkali resistance based on the antibody binding capacity after the alkali treatment.

The affinity separation matrices used were the prototype 4 of Table 6 obtained in Example 10, and the prototypes 5 to 7 (and comparison 3) of Table 11 obtained in Example 13. A cycle consisting of running 0.5 M NaOH at 0.1 mL/min for 1 hour, and running 5 CV of a standard buffer for equilibration was repeated 5 times, and then the same procedure as in Example 6 was performed to determine the antibody dBC. Table 12 is provided for comparison of the antibody dBC values measured before and after the alkali treatment.

TABLE 12

| Prototype ID | Number of Lys in ligand [number of residues] | 5% antibody dBC [mg/mL-gel] Before alkali treatment | 5% antibody dBC [mg/mL-gel] After alkali treatment | 5% antibody dBC Remaining percentage [%] |
|---|---|---|---|---|
| Comparison 3 | 14 | 23.4 | 22.7 | 97.0 |
| Prototype 4 | 1 (C terminal) | 28.3 | 27.4 | 96.8 |
| Prototype 5 | 1 (C terminal) | 27.4 | 26.0 | 94.9 |
| Prototype 6 | 1 (C terminal) | 29.2 | 27.8 | 95.2 |
| Prototype 7 | 1 (C terminal) | 30.5 | 28.9 | 94.8 |

Immobilized ligand
Comparison 3: C-G29A/S33E.2d_type.2
Prototype 4: C-K04R/K07R/G29A/K35R/K42R/K49R/K50R/K58R.2d_type2
Prototype 5: C-K04R/K07R/G29A/S33E/K35R/K42R/K49R/K50R/K58R.2d_type2
Prototype 6: C-K04R/K07D/G29A/S33L/K35R/K42R/K49R/K50R/K58R.2d_type2
Prototype 7: C-K04R/K07E/G29A/K35R/D36I/K42R/K49R/K50R/K58R.2d_type2

The results revealed that the affinity separation matrices of the present invention, even when treated with 0.5 M NaOH for 5 hours, showed only a small reduction in the antibody binding capacity of 10% or less. As described in Patent Literature 2, it has been believed that affinity separation matrices in which a ligand is immobilized through the amino group of lysine have higher chemical resistance to, for example, alkali when they have more lysine residues involving immobilization. On the contrary, the prototype matrices 4 to 7, the ligand of which contained only one immobilization site, were found to have a similar level of alkali resistance to the comparison matrix 3, the ligand of which contained 14 immobilization sites.

Example 15

Preparation and Evaluation Three-domain Type C Domain Variant

A DNA (SEQ ID No:95) encoding C-K04R/K07R/G29A/S33L/K35R/K42R/K49R/K50R/K58R.3d_type2 (Lys-58 in the most C-terminal domain (third domain) was conserved) (SEQ ID No:94) and containing an additional NcoI recognition site at the 5' terminal and an additional XbaI recognition site at the 3' terminal was entirely synthesized by an external institution (Eurogentec).

Also, a DNA (SEQ ID No:97) encoding C-K04R/K07R/G29A/S33L/K35R/K42R/K49R/K50R.3d_type2 (SEQ ID No:96) that contains Lys at the C terminal of this ligand, and Lys at the C terminal of the first and second domains as counted from the N terminal (in linkers between domains) was entirely synthesized by an external institution.

Then, these DNAs were inserted into the expression vector pNK3260' for expression in Brevibacillus to prepare a ligand expression plasmid. The vector pNK3260' is able to accept insertion not only at the PstI/EcoRI site but also at the NcoI/XbaI site (Takara Bio, Inc.).

This expression plasmid was transformed into Brevibacillus choshinensis FY-1, and an affinity separation matrix in which the ligand was immobilized on a carrier was prepared in the same manner as in Example 5. This prototype affinity separation matrix was evaluated for the binding ability to human IgG in the same manner as in Example 6, except that the human IgG solution was run at 1.0 mL/min. The results are shown in Table 13. The affinity constants for human IgG shown in the table were obtained in accordance with Example 3, and the ligand immobilized amounts were obtained in accordance with Example 5.

TABLE 13

| Prototype ID | Number of Lys in ligand [number of residues] | Antibody affinity constant $K_A$ [×10$^8$M$^{-1}$] | Ligand immobilized amount [mg/mL-gel] | 5% antibody dBC [mg/mL-gel] |
|---|---|---|---|---|
| Prototype 8 | 1 | 22 | 9.4 | 36.9 |
| Prototype 9 | 3 | 21 | 8.6 | 38.5 |

Immobilized ligand
Prototype 8: C-K04R/K07R/G29A/S33L/K35R/K42R/K49R/K50R/K58R.3d_type2
Prototype 9: C-K04R/K07R/G29A/S33L/K35R/K42R/K49R/K50R.3d_type2

The three-domain type C domain variant was also found to have a high antibody dBC. It was also found that a ligand immobilized through its C terminal shows a high antibody dBC even when its linker sites between domains also involve in the immobilization.

Comparative Example 1

C-G29A and C-G29A/S33E

Expression plasmids for C-G29A.1d, C-G29A.2d, C-G29A/S33E.1d, C-G29A.4d, and C-G29A/S33E.2d were prepared in accordance with the description in Patent Literature (WO 2010/110288). The detail is omitted except the following procedures not described in the literature.

(1) The expression plasmid for C-G29A.1d was prepared by inserting a coding DNA into pGEX-2T.
(2) The mutation S33E was introduced by quick change mutagenesis.
(3) The expression plasmids for the two-domain type and the four-domain type were prepared as follows: PCR was performed using an expression plasmid for the five-domain type as a template to amplify only a region corresponding to the desired number of domains; and the amplified product was re-inserted into the vector pNK3260'.

C-G29A.1d was prepared by transforming the expression plasmid into HB101, and performing the same procedure as in Example 2. Their binding ability to human IgG was evaluated in the same manner as in Example 3. C-G29A/S33E.1d, C-G29A.2d, C-G29A.4d, and C-G29A/S33E.2d were respectively prepared using corresponding expression plasmids in the same manner as in Example 4. Prototype carriers with the ligands immobilized thereon were prepared in the same manner as in Example 5, and prototype affinity separation matrices were evaluated for the binding ability to human IgG in the same manner as in Example 6. Not all the ligand solutions used for the preparation of the prototype affinity separation matrices had a concentration of 10 mg/mL.

The invention claimed is:

1. A protein comprising an amino acid sequence obtained by introducing amino acid substitutions for all Lys (lysine) residues, and adding Lys to a terminus, into the amino acid sequence derived from the C domain of protein A having the amino acid sequence of SEQ ID No:5,
wherein not less than half of the amino acid substitutions for all the Lys residues are substitutions of Arg,
wherein 90% or more of Gln-9, Gln-10, Phe-13, Tyr-14, Leu-17, Pro-20, Asn-21, Leu-22, Gln-26, Arg-27, Phe-30, Ile-31, Leu-34, Pro-38, Ser-39, Leu-45, Leu-51, Asn-52, Gln-55, and Pro-57 are conserved in the protein wherein the residue numbers correspond to the residue numbers of the C domain of SEQ ID No:5,
the protein has at least 80% sequence identity to the full length amino acid sequence of SEQ ID No:5, and
wherein the protein is immobilized on a carrier of an affinity separation matrix through the Lys added to the terminus.

2. A multi-domain protein wherein two or more of the proteins according to claim 1 are connected together.

3. The protein according to claim 1, wherein all the substitutions are substitutions of Arg.

4. The protein according to claim 2, wherein two or more of the domains of the Protein A are linked to one another through a linker.

5. The protein according to claim 4, wherein the linker comprises Lys.

6. An affinity separation matrix comprising: a protein according to claim 1 as an affinity ligand; and a carrier made of a water-insoluble base material on which the protein is immobilized.

7. The affinity separation matrix according to claim 6, which binds to a protein comprising an Fc region of an immunoglobulin.

8. A DNA encoding a protein according to claim 1.

9. A vector comprising a DNA according to claim 8.

10. A transformant obtainable by transforming a vector according to claim 9 into a host cell.

11. A method for producing a protein according to claim 1 which comprises:
using either a cell-free protein synthesis system incorporating a DNA encoding said protein according to claim 9 or a transformant according to claim 10.

12. A method for preparing an affinity separation matrix, the method comprising:
immobilizing a protein according to claim 1 on a carrier made of a water-insoluble material.

13. A method for purifying a protein containing an Fc region of an immunoglobulin, the method comprising:
adsorbing a protein containing an Fc region of an immunoglobulin to an affinity separation matrix according to claim 6.

* * * * *